United States Patent
Hyde et al.

(10) Patent No.: US 10,232,165 B2
(45) Date of Patent: *Mar. 19, 2019

(54) GARMENT SYSTEM INCLUDING AT LEAST ONE SENSOR AND AT LEAST ONE ACTUATOR RESPONSIVE TO THE SENSOR AND RELATED METHODS

(71) Applicant: Elwha LLC, Bellevue, WA (US)

(72) Inventors: Roderick A. Hyde, Redmond, WA (US); Muriel Y. Ishikawa, Livermore, CA (US); Jordin T. Kare, San Jose, CA (US); Max N. Mankin, Cambridge, MA (US); Nathan P. Myhrvold, Bellevue, WA (US); Tony S. Pan, Bellevue, WA (US); Robert C. Petroski, Seattle, WA (US); Elizabeth A. Sweeney, Seattle, WA (US); Clarence T. Tegreene, Mercer Island, WA (US); Nicholas W. Touran, Seattle, WA (US); Yaroslav A. Urzhumov, Bellevue, WA (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 745 days.

This patent is subject to a terminal disclaimer.

(21) Appl. No.: 14/609,409

(22) Filed: Jan. 29, 2015

(65) Prior Publication Data

US 2016/0220808 A1    Aug. 4, 2016

(51) Int. Cl.
*A61H 23/02*  (2006.01)
*A61N 1/04*   (2006.01)
(Continued)

(52) U.S. Cl.
CPC .......... *A61N 1/0452* (2013.01); *A61B 5/6804* (2013.01); *A61B 5/6895* (2013.01);
(Continued)

(58) Field of Classification Search
CPC ............ A61H 1/008; A61H 2201/1207; A61H 2201/1238; A61H 7/00; A61H 7/007;
(Continued)

(56) References Cited

U.S. PATENT DOCUMENTS

| 4,311,838 A | 1/1982 | Davis et al. |
| 5,179,941 A | 1/1993 | Siemssen et al. |

(Continued)

FOREIGN PATENT DOCUMENTS

| CA | 2 332 747 A1 | 4/2001 |
| CN | 101039641 A | 9/2007 |

(Continued)

OTHER PUBLICATIONS

PCT International Search Report; International App. No. PCT/US2015/057954; dated Feb. 4, 2016; pp. 1-4.
(Continued)

*Primary Examiner* — Steven O Douglas
(74) *Attorney, Agent, or Firm* — Dorsey & Whitney LLP

(57) ABSTRACT

Embodiments disclosed herein relate to a garment system including at least one sensor and at least one actuator that operates responsive to sensing feedback from the at least one sensor to cause a flexible compression garment to selectively constrict or selectively dilate, thereby compressing or relieving compression against at least one body part of a subject. Such selective constriction or dilation can improve muscle functioning or joint functioning during use of motion-conducive equipment, such as an exercise bike or rowing machine.

56 Claims, 13 Drawing Sheets

(51) Int. Cl.
  *A61H 9/00* (2006.01)
  *A61H 11/00* (2006.01)
  *A61B 5/00* (2006.01)
  *A61B 5/11* (2006.01)
  *A61H 3/04* (2006.01)
  *A61B 5/01* (2006.01)
  *A61B 5/021* (2006.01)
  *A61B 5/024* (2006.01)
  *A61B 5/04* (2006.01)
  *A61B 5/0488* (2006.01)
  *A61B 5/103* (2006.01)
  *A61B 5/145* (2006.01)

(52) U.S. Cl.
  CPC ............ *A61H 9/0078* (2013.01); *A61H 11/00* (2013.01); *A61B 5/01* (2013.01); *A61B 5/021* (2013.01); *A61B 5/024* (2013.01); *A61B 5/04001* (2013.01); *A61B 5/0488* (2013.01); *A61B 5/1036* (2013.01); *A61B 5/112* (2013.01); *A61B 5/1112* (2013.01); *A61B 5/1118* (2013.01); *A61B 5/14542* (2013.01); *A61B 2503/10* (2013.01); *A61H 2003/043* (2013.01); *A61H 2011/005* (2013.01); *A61H 2201/0207* (2013.01); *A61H 2201/0214* (2013.01); *A61H 2201/0242* (2013.01); *A61H 2201/1207* (2013.01); *A61H 2201/165* (2013.01); *A61H 2201/5035* (2013.01); *A61H 2201/5058* (2013.01); *A61H 2201/5061* (2013.01); *A61H 2201/5084* (2013.01); *A61H 2205/06* (2013.01); *A61H 2205/08* (2013.01); *A61H 2205/10* (2013.01); *A61H 2209/00* (2013.01); *A61H 2230/00* (2013.01); *A61H 2230/208* (2013.01); *A61H 2230/505* (2013.01); *A61H 2230/605* (2013.01)

(58) Field of Classification Search
  CPC ........ A61H 7/008; A61H 9/00; A61H 9/0157; A61H 9/02; A61H 9/0207; A61H 9/0214; A61H 9/50; A61H 9/5058; A61H 9/5071; A61H 9/0078; A61H 11/00; A61H 2003/043; A61H 2011/005; A61H 2201/0242; A61H 2201/165; A61H 2201/2201; A61H 2201/5035; A61H 2201/5061; A61H 2201/5084; A61H 2205/06; A61H 2205/08; A61H 2205/10; A61H 2209/00; A61N 1/0452; A61B 5/6895; A61B 5/6804; A61B 5/112; A61B 5/01; A61B 5/21; A61B 5/024; A61B 5/04001; A61B 5/0488; A61B 5/1036
  See application file for complete search history.

(56) References Cited

U.S. PATENT DOCUMENTS

| | | | |
|---|---|---|---|
| 5,218,954 A * | 6/1993 | van Bemmelen | A61H 9/0078 128/DIG. 20 |
| 5,396,896 A | 3/1995 | Tumey et al. | |
| 5,997,465 A | 12/1999 | Savage et al. | |
| 6,262,014 B1 | 7/2001 | Kohama et al. | |
| 6,494,852 B1 * | 12/2002 | Barak | A61F 5/012 601/148 |
| 7,056,297 B2 * | 6/2006 | Dohno | A63B 21/00181 310/316.01 |
| 7,491,185 B2 | 2/2009 | Couvillon, Jr. | |
| 8,079,969 B2 | 12/2011 | Rousso et al. | |
| 8,360,904 B2 | 1/2013 | Oleson et al. | |
| 8,577,471 B2 | 11/2013 | Stuerzinger et al. | |
| 8,581,731 B2 | 11/2013 | Purks et al. | |
| 8,734,369 B2 | 5/2014 | Perry et al. | |
| 8,753,300 B2 | 6/2014 | Deshpande | |
| 8,758,282 B2 | 6/2014 | Malhi et al. | |
| 8,764,689 B2 | 7/2014 | Toth | |
| 9,687,404 B2 * | 6/2017 | Cheatham, III | A61H 1/008 |
| 9,717,642 B2 * | 8/2017 | Deshpande | A61H 9/0007 |
| 2003/0120183 A1 | 6/2003 | Simmons | |
| 2005/0060030 A1 | 3/2005 | Lashinski et al. | |
| 2005/0154336 A1 | 7/2005 | Kloecker et al. | |
| 2006/0058694 A1 | 3/2006 | Clark et al. | |
| 2006/0122544 A1 | 6/2006 | Ciluffo | |
| 2007/0049853 A1 | 3/2007 | Adams et al. | |
| 2007/0129776 A1 | 6/2007 | Robins et al. | |
| 2007/0265140 A1 * | 11/2007 | Kim | A61H 1/02 482/8 |
| 2008/0214971 A1 * | 9/2008 | Talish | A61H 1/005 601/23 |
| 2008/0215114 A1 | 9/2008 | Stuerzinger et al. | |
| 2008/0319359 A1 | 12/2008 | Moomiaie-Qajar et al. | |
| 2009/0036938 A1 | 2/2009 | Shipley et al. | |
| 2009/0234262 A1 | 9/2009 | Reid, Jr. et al. | |
| 2009/0234265 A1 | 9/2009 | Reid, Jr. et al. | |
| 2010/0056966 A1 | 3/2010 | Toth | |
| 2010/0305484 A1 | 12/2010 | Grollier et al. | |
| 2011/0015498 A1 | 1/2011 | Mestrovic et al. | |
| 2011/0066091 A1 | 3/2011 | Larson et al. | |
| 2011/0066093 A1 | 3/2011 | Vess | |
| 2011/0092337 A1 | 4/2011 | Srivasan et al. | |
| 2011/0120567 A1 * | 5/2011 | Kuehne | A63B 21/00181 137/14 |
| 2012/0065561 A1 | 3/2012 | Ballas et al. | |
| 2012/0071743 A1 | 3/2012 | Todorov et al. | |
| 2012/0078145 A1 | 3/2012 | Malhi et al. | |
| 2012/0078146 A1 | 3/2012 | Deshpande | |
| 2012/0083712 A1 | 4/2012 | Watson et al. | |
| 2012/0089063 A1 | 4/2012 | Olson et al. | |
| 2012/0130203 A1 | 5/2012 | Stergiou et al. | |
| 2012/0143514 A1 | 6/2012 | Vock et al. | |
| 2012/0203132 A1 | 8/2012 | Blumensohn et al. | |
| 2012/0289870 A1 | 11/2012 | Hsiao-Wecksler et al. | |
| 2013/0041235 A1 | 2/2013 | Rogers et al. | |
| 2013/0072301 A1 | 3/2013 | Mallinson | |
| 2013/0158444 A1 | 6/2013 | Herr et al. | |
| 2013/0211259 A1 | 8/2013 | Komistek et al. | |
| 2013/0289456 A1 | 10/2013 | Chang Guo et al. | |
| 2013/0310719 A1 | 11/2013 | Davis et al. | |
| 2013/0345610 A1 * | 12/2013 | Larson | A61B 17/1325 601/134 |
| 2014/0019063 A1 | 1/2014 | McHugh et al. | |
| 2014/0070957 A1 | 3/2014 | Longinotti-Buttoni et al. | |
| 2014/0135593 A1 | 5/2014 | Jayalth et al. | |
| 2014/0140567 A1 | 5/2014 | LeBoeuf et al. | |
| 2014/0142459 A1 | 5/2014 | Jayalth et al. | |
| 2014/0163444 A1 | 6/2014 | Ingvarsson et al. | |
| 2014/0194795 A1 | 7/2014 | Wild et al. | |
| 2014/0207036 A1 | 7/2014 | Perry et al. | |
| 2014/0213940 A1 | 7/2014 | Mayer | |
| 2014/0276283 A1 | 9/2014 | Mansur, Jr. et al. | |
| 2014/0330186 A1 | 11/2014 | Hyde et al. | |
| 2015/0073907 A1 | 3/2015 | Purves et al. | |
| 2015/0297437 A1 | 10/2015 | Neuenhahn et al. | |
| 2015/0351690 A1 | 12/2015 | Toth et al. | |
| 2016/0015280 A1 | 1/2016 | Hyde et al. | |

FOREIGN PATENT DOCUMENTS

| | | |
|---|---|---|
| WO | WO 2013/033669 A2 | 3/2013 |
| WO | WO 2014/041032 A1 | 3/2014 |
| WO | WO 2014/066077 A1 | 5/2014 |

OTHER PUBLICATIONS

U.S. Appl. No. 14/529,046, filed Oct. 30, 2014, Ishikawa, et al.
Kim, et al. "Epidermal Electronics" Science 333, 838-843 (2011).
Hamaoka, et al. "The use of muscle near-infrared spectroscopy in sport, health and medical sciences: recent developments", Phil. Trans. R. Soc. A (2011) 369, 4591-4604.

(56) References Cited

OTHER PUBLICATIONS

Harrison, et al. "Portable acoustic myography—a realistic noninvasive method for assessment of muscle activity and coordination in human subjects in most home and sports settings" Physiological Reports, vol. 1, Issue 2: e00029, pp. 1-9 (2013).

Chen, et al. "A brief review of actuation at the micro-scale using electronics, electromagnetics and piezoelectric ultrasonics" Acoust. Sci. & Tech. 31, 2 (2010).

Vanhemert "Coming Soon: Workout Gear That Monitors Your Muscles" Dec. 4, 2013; Wired, 4 pages, http://www.wired.com/2013/12/these-smart-gym-clothes-are-the-future-of-wearable-computers/.

New Scale Technologies "Squiggle micro motor technology: Patented piezoelectric motor with small size, high force speed" Available as of Aug. 26, 2014, 3 pages. http://www.newscaletech.com/technology/squiggle-motors.php.

New Scale Technologies, Thomasnet.com "New Drive Solutions for Squiggle® Micro Motors Add Speed Control Options, Dynamic Optimization of Motor Performance over Temperature" Jul. 21, 2009, 2 pages. http://news.thomasnet.com/companystory/New-Drive-Solutions-for-SQUIGGLE-Micro-Motors-Add-Speed-Control-Options-Dynamic-Optimization-of-Motor-Performance-over-Temperature-828373.

PI, www.pi.ws "Piezo Motor Solutions for Automation & Ultra-Precision Motion Control" Available as of Aug. 26, 2014, 4 pages. http://www.piezo-motor.net/piezo-motor_ultrasonic_and_ultra-precision_stepping.htm.

PI, www.pi.ws "PILine Ultrasonic Piezomotor Working Principle" Available as of Aug. 26, 2014, 2 pages http://www.physikinstrumente.com/en/products/piezo_motor/piline.php.

PCT International Search Report; International App. No. PCT/US2018/018115; dated Jun. 27, 2018; pp. 1-5.

European Patent Office, Supplementary European Search Report, Pursuant to Rule 62 EPC; App. No. EP 15855573; dated May 25, 2018 (recieved by our Agent on Jun. 8, 2018); pp. 1-12.

European Patent Office, Extended European Search Report, Pursuant to Rule 62 EPC; App. No. EP 15 82 6158; dated Mar. 21, 2018; pp. 1-7.

Chinese State Intellectual Property Office, Notification of First Office Action, App. No. 201580057646.6 (based on PCT Patent Application No. PCT/2015/046717); dated Nov. 29, 2018; pp. 1-13 (machine translation provided).

\* cited by examiner

GARMENT SYSTEM INCLUDING AT LEAST ONE SENSOR AND AT LEAST ONE ACTUATOR RESPONSIVE TO THE SENSOR AND RELATED METHODS

BACKGROUND

Compression garments including clothing articles, such as socks, arm sleeves, leg sleeves, etc., can provide support to muscles of a body part on which the compression garments are worn. This support can be useful for people who have to stand for long periods, or people with circulation problems.

Compression sportswear, which is a specific type of compression garment, can also be worn by athletes during exercise. For example, bicycling shorts are a common type of compression sportswear. Compression sportswear can improve muscle functioning, and prevent chafing and rashes during and after exercise.

Compression garments are believed to have a number of positive effects on a user. For example, compression garments can help relieve pain from muscle stiffness and soreness, and reduce time taken for muscles to repair themselves. Also, when an appropriate amount of compression is used, compression garments can improve venous return and oxygenation to working muscles.

SUMMARY

Embodiments disclosed herein relate to a garment system including at least one sensor disposed on or in a piece of motion-conducive equipment and at least one actuator associated with a flexible compression garment that operates responsive to sensing feedback from the at least one sensor to cause the flexible compression garment to selectively constrict or selectively dilate, thereby selectively compressing against or selectively relieving compression against at least one body part of a subject. Such selective constriction or dilation can improve muscle functioning or joint functioning during use of motion-conducive equipment, such as an exercise bike or a rowing machine.

In an embodiment, a garment system is disclosed. The garment system includes at least one flexible compression garment configured to be worn on at least one body part of a subject. The at least one flexible compression garment defines an interior space configured to receive the at least one body part. The garment system includes motion-conducive equipment. The garment system includes one or more sensors disposed on or in the motion-conducive equipment. The one or more sensors are configured to sense at least one characteristic associated with movement of the subject or at least one physiological characteristic of the subject. The one or more sensors are further configured to output one or more sensing signals indicative of the at least one characteristic. The garment system further includes one or more actuators positioned relative to the at least one flexible compression garment and configured to selectively constrict or selectively dilate the at least one flexible compression garment. The garment system additionally includes a control system operably coupled to the one or more actuators and further operably coupled to the one or more sensors to receive the one or more sensing signals therefrom. The control system includes control electrical circuitry configured to direct the one or more actuators to selectively constrict or selectively dilate the at least one flexible compression garment responsive to the one or more sensing signals from the one or more sensors.

In an embodiment, a method of selectively controlling a compression garment is disclosed. The method includes sensing at least one characteristic of a subject moving on at least one piece of motion-conducive equipment using one or more sensors associated therewith. The method includes comparing the sensed at least one characteristic to a threshold characteristic. The method further includes responsive to comparing the at least one characteristic, actuating one or more actuators in at least one flexible compression garment worn on the subject to selectively constrict or selectively dilate on at least one body part of the subject.

Features from any of the disclosed embodiments may be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
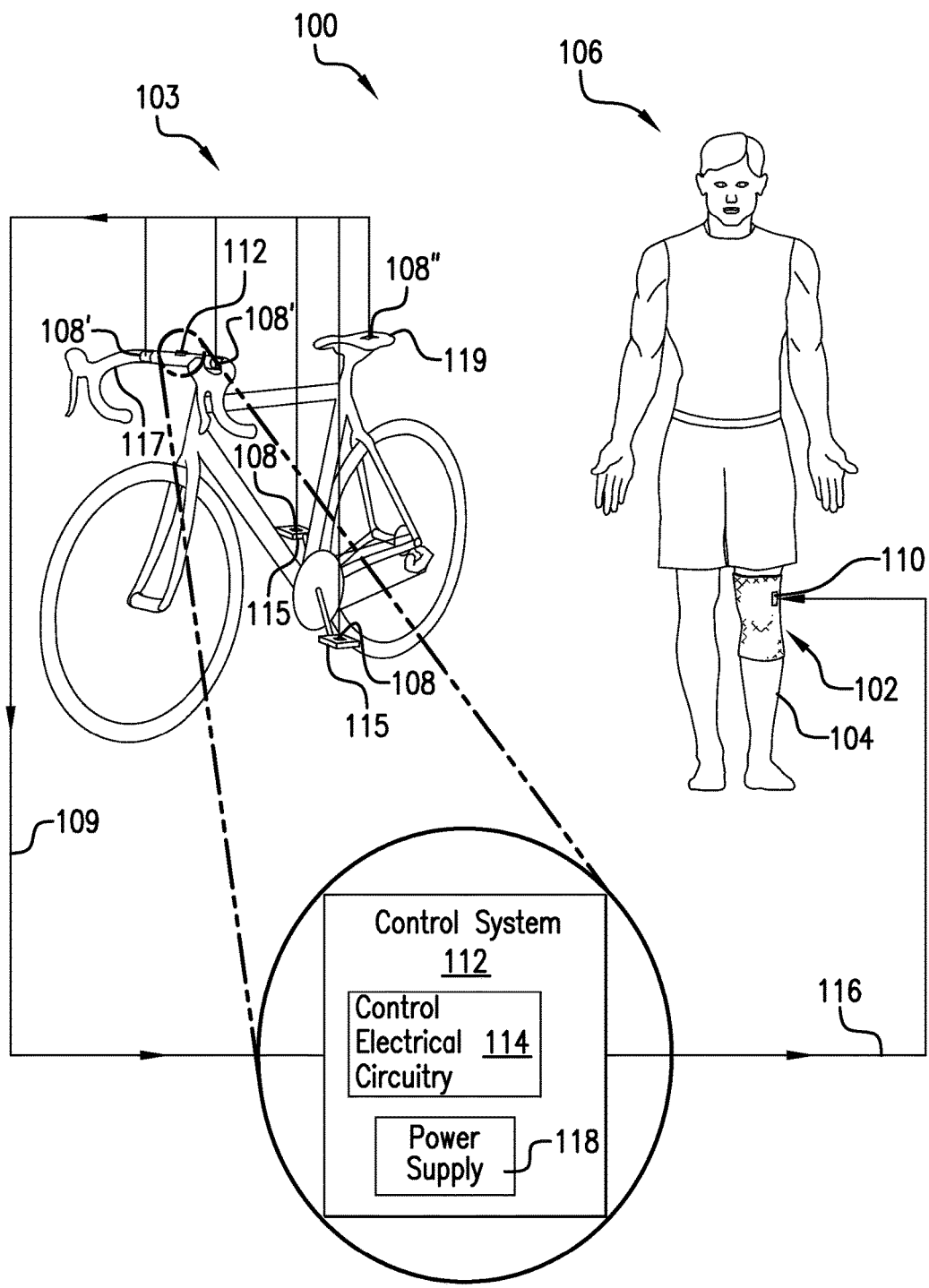
FIG. 1A is a diagrammatic view of a garment system according to an embodiment.

Embodiments disclosed herein relate to a garment system including at least one sensor disposed on or in a piece of motion-conducive equipment and at least one actuator associated with a flexible compression garment that operates responsive to sensing feedback from the at least one sensor to cause the flexible compression garment to selectively constrict or selectively dilate, thereby selectively compressing against or selectively relieving compression against at least one body part of a subject. Such selective constriction or dilation can improve muscle functioning or joint functioning during use of motion-conducive equipment, such as an exercise bike or a rowing machine.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1A illustrates a garment system 100 according to an embodiment. The garment system 100 includes a flexible compression garment 102 that is configured to be worn on at least one body part 104 of a subject 106 during use. The garment system 100 includes one or more sensors 108 supported by a piece of motion-conducive equipment 103. The one or more sensors are configured to sense at least one characteristic associated with movement of the subject or at least one physiological characteristic of the subject. The garment system 100 further includes one or more actuators 110 positioned relative to the flexible compression garment 102 and configured to selectively constrict or selectively dilate the flexible compression garment 102 about the at least one body part 104, thereby selectively compressing against or selectively relieving compression against at least one body part 104.

The garment system 100 further includes a control system 112 operably coupled to the one or more sensors 108 and the one or more actuators 110, and configured to receive one or more sensing signals 109 (carrying sensing data) from the one or more sensors 108 and send one or more actuation signals 116 to the one or more actuators 110 to direct actuation thereof responsive to the sensing signals 109. The control system 112 includes control electrical circuitry 114 and a power supply 118 for powering one or more of the one or more sensors 108, the one or more actuators 110, or the control system 112 itself.

The flexible compression garment 102 can be substantially tubular and configured to generally conform to the at least one body part 104 when worn thereon. For example, the flexible compression garment 102 can be made from any suitable material. More specifically, for example, the flexible compression garment 102 can be made from neoprene, nylon, synthetic rubber, or any other suitable synthetic or natural fabric or polymeric material.

In the illustrated embodiment, the at least one body part 104 is a leg of the subject 106, which can include one or more of a portion of the subject's 106 upper leg such as the thigh, lower leg such as the calf, or knee joint therebetween that is received by the flexible compression garment 102. However, as discussed in more detail below, the garment systems disclosed herein can be employed on many other types of body parts. For example, the at least one body part 104 of the subject 106 can include one or more of at least a portion of an upper arm, forearm, an elbow joint therebetween, a wrist, a hand, a foot, a neck, a head, a hip, a torso, or at least a portion of any of the foregoing. As another example, the flexible compression garment 102 can be configured as a shirt, and the at least one body part 104 includes at least a portion of the chest or abdomen of the subject 106. Thus, in some embodiments, the flexible compression garment 102 can be configured as a limb sleeve (e.g., arm or leg sleeve), a joint sleeve (e.g., elbow, knee, ankle, wrist, or finger sleeve), a shirt, a vest, a jacket, an undershirt, a girdle, an abdominal support, back support, gloves, shorts, pants, or socks.

The one or more sensors 108 can be associated with the motion-conducive equipment 103, such as at least partially embedded in or disposed on one or more portions of the motion-conducive equipment (e.g., pedals of a bicycle as shown in FIG. 1A). For example, the one or more sensors can be mounted on, embedded in, or otherwise supported by the motion-conducive equipment 103. The one or more sensors 108 are positioned and configured in or on the motion-conducive equipment 103 to sense or detect at least one characteristic associated with movement of the subject or at least one physiological characteristic of the subject. For example, each or some of the one or more sensors 108 can be positioned adjacent to or proximate to at least one position of placement of at least one foot (e.g., on a foot rest, tread deck, or pedal), a torso of the subject 106, a gluteus maximus of the subject 106 (e.g., on a seat), or position of placement of at least one hand (e.g., on a handle, grip, or bar) of the subject 106 to monitor at least one characteristic associated with movement of the subject or at least one physiological characteristic of the subject. In an embodiment, the one or more sensors 108 can be disposed on or in a portion of the motion-conducive equipment 103 not associated with a body part of the subject 106. For example, the one or more sensors 108 can be disposed on a support member in the motion-conducive equipment 103, on a pulley in the motion-conducive equipment 103, on a controller of the motion-conducive equipment 103, on a wheel, or on any other suitable portion of the motion-conducive equipment 103. During use, the one or more sensors 108 output the one or more sensing signals 109 (e.g., signals from the one or more sensors) indicative of the at least one characteristic. It is noted that the at least one characteristic associated with movement of the subject 106 or at least one physiological characteristic of the subject 106 to be sensed can involve a plurality of muscles or a plurality joints. For example, in the case where the flexible compression garment 102 receives at least a portion of an upper leg and at least a portion of a lower leg of the subject 106, at least one muscle of the at least one body part 104 can include a plurality of muscles in each of the upper leg and lower leg of the at least one body part 104 and the at least one joint of the at least one body part 104 can include the knee joint.

In an embodiment, one or more sensors 108, 108', or 108" can be positioned on the motion-conducive equipment 103, such as at or near a tread deck or foot rest 115 (e.g., pedal as shown), at or near a handle 117 or support, at or near a seat 119, or at or near any other position suitable to sense or detect the desired at least one characteristic. In an embodiment, the one or more sensors 108 can be positioned on the motion-conducive equipment 103 proximate to the at least one body part 104 on which the at least one flexible compression garment 102 is configured to be worn. For example, as shown in FIG. 1A, sensor 108 can be positioned on the left pedal of a bicycle while the flexible compression garment 102 is worn on the left leg of the subject 106. In an embodiment, the sensor 108 can be disposed on a portion of the motion-conducive equipment 103 not adjacent to the at least one body part 104 on which the at least one flexible compression garment 102 is configured to be worn (e.g., adjacent to a separate or distinct body part from the at least one body part 104). For example, the one or more sensors 108 can be disposed on one or more pedals and the flexible compression garment 102 can be configured as an arm sleeve. In an embodiment, the one or more sensors 108 can be positioned without regard to the at least one body part 104, such as in a pulley of a rowing machine or in a wheel of a bicycle.

The one or more actuators 110 are positioned relative to the flexible compression garment 102 and configured to cause the flexible compression garment 102 to selectively constrict or selectively dilate the flexible compression garment 102, thereby selectively compressing or selectively relieving compression against the at least one body part 104 responsive to the one or more sensing signals 109 output by the one or more sensors 108. For example, the one or more actuators 110 can be embedded in the flexible compression garment 102, mounted interiorly inside of the flexible compression garment 102 in an interior space thereof in which the at least one body part 104 is received, or mounted exteriorly on the flexible compression garment 102.

As discussed above, the control system 112 (e.g., a computer control system) is operably coupled to the one or more sensors 108 and the one or more actuators 110. For example, the control system 112 can be wirelessly operably coupled to the one or more sensors 108 or the one or more actuators 110. As another example, the control system 112 can be operably coupled to the one or more sensors 108 or the one or more actuators 110 via a wired connection, such as physical electrical wiring. The control system 112 or portions thereof can be mounted to, embedded in, or housed on the motion-conducive equipment 103 as shown in FIG. 1A. In an embodiment, at least a portion of the control system 112 can also be operably coupled to and control the motion-conducive equipment 103. For example, the control system 112 can be operably coupled to the motion-conducive equipment 103 via a wireless or wired connection. In such an embodiment, the control system 112 can receive indication signals from the motion-conducive equipment regarding movement properties (e.g., resistance, speed of movement, angle of incline, path of movement, etc.) or changes therein dictated by the motion-conducive equipment 103. In an embodiment, the control system 112 can control the operation of the motion-conducive equipment 103, such as by maintaining, increasing, or decreasing movement properties responsive to sensing signals. The control system 112 can be sized and configured to be conveniently worn or carried by the subject 106, such as via the at least one flexible compression garment 102, or on yet another body part such as in or on a wearable device 113 (e.g., a strap, wrap, article of clothing, garment, or belt shown in FIG. 1B) worn around a waist, chest, arm, hand, leg, foot, or head, of the subject.

The power supply 118 of the control system 112 can include at least one of a wired connection to a power outlet (e.g., a wall plug, a plug into an motion-conducive equipment 103 which supplies power, or hardwiring to an motion-conducive equipment 103 which supplies power), one or more batteries, a stretchable/flexible power supply, a fuel cell, an energy harvester, a solar energy harvester, a kinetic energy harvester, a triboelectric nanogenerator, or other suitable power supply. For example, in an embodiment, the power supply 118 can be housed separately from the rest of the control system 112 including the control electrical circuitry 114. Suitable batteries for use as the power supply 118 include one or more of a microbattery, an alkaline battery, a lithium ion battery, a coin battery, a watch battery, a button battery, a zinc-air battery, a thin film battery, a flexible battery, or any other suitable battery. The power supply 118 can be operably coupled to and configured to provide power (e.g., voltage or current) to at least some of the components of the garment system 100, such as one or more of the control electrical circuitry 114, the one or more sensors 108, or the one or more actuators 110.

In an embodiment, the power supply 118 can be stored or housed separately from the control electrical circuitry 114. In an embodiment, the power supply 118 can be stored or housed separately from the one or more actuators 110 or one or more sensors 108. In an embodiment, the power supply 118 can be stored or housed on the motion-conducive equipment 103. In an embodiment the power supply 118 can be stored or housed on a separate part of the body of the subject 106 than the control electrical circuitry 114, one or more actuators 110, or one or more sensors 108. In an embodiment, the power supply 118 can include a wireless power supply, such as a power supply configured to supply power via induction (e.g., direct or resonant magnetic induction).

In an embodiment, the power supply 118 is rechargeable. For example, motion-conducive equipment 103 can include a charging port operably coupled to the power supply 118 and configured recharge the power supply 118. In an embodiment, one or more of the motion-conducive equipment 103 or the at least one flexible compression garment 102 can include one or more energy harvesting devices. Energy harvesting devices can include a photovoltaic cell, a thermoelectric generator, a piezoelectric devices (e.g., piezoelectric crystals or piezoelectric generators), or a kinetic energy harvester (e.g., a spring wound using kinetic energy). For example, the motion-conducive equipment 103 can include a kinetic energy harvesting device associated with (e.g., affixed to, secured to, or attached to) a portion thereof. In an embodiment, the portion may be a tread deck such as a pedal on an exercise bike or handle on a rowing machine, where the kinetic energy harvesting device converts the kinetic energy of the motion of the pedal or handle into electrical energy to power one or more portions of the motion-conducive equipment 103 or the at least one flexible compression garment 102, including one or more of any components thereof. In an embodiment, the at least one flexible compression garment 102 can include a kinetic energy harvesting device therein, whereby conversion of the kinetic energy from the motion of a swinging arm or leg can provide the electrical energy to power into electrical energy to power one or more portions of the motion-conducive equipment 103 or the at least one flexible compression garment 102, including one or more of any components thereof.

The control system 112 including any parts thereof can be configured to be removably disposed on the motion-conducive equipment 103 or the subject 106. For example, one or more of the control electrical circuitry 114, the one or more sensors 108, or the power supply 118 can be configured in a modular format, such as replaceable or changeable sensors 108. One or more of the control electrical circuitry 114 or the one or more sensors 108 can be configured to directly or indirectly interface with a computing device. For example, the control electrical circuitry 114 can be configured to be removably disposed on the motion-conducive equipment 103, and the control electrical circuitry 114 is also configured to interface, either directly or indirectly, with a computing device, such as by a hard connection (e.g., USB connection) or wireless port on the thereon. In an embodiment, at least one of the control electrical circuitry 114 or the one or more sensors 108 are further configured to upload or download one or more of at least one operational program, selected profile, threshold level, or sensing data to or from the computing device.

In an embodiment, the one or more sensors 108 can be removably disposed on or at least partially embedded within a portion of the motion-conducive equipment 103. For example, the one or more sensors 108 can be modular, such as replaceable or changeable sensors. In an embodiment, at least one of the modular one or more sensors 108 can be removed from the motion-conducive equipment 103 and be replaced with an identical sensor or an additional, different type of sensor. For example, a modular pressure sensor and a modular timer on a handle can be removed and be replaced with a modular altimeter and modular chemical sensor.

One or more operational programs that the control electrical circuitry 114 of the control system 112 employs for directing and controlling the operation of the one or more sensors 108 and the one or more actuators 110 can be pre-programmed in the control electrical circuitry 114, or programmed by the subject 106 or other person such as a medical professional like a doctor, a nurse, a physical therapist, a trainer, etc. For example, the programming of the control electrical circuitry 114 can be affected via at least one of software, firmware, programmable logical devices, or other technique for controlling the one or more sensors 108 and the one or more actuators 110 or other components of the garment system 100 in a selected manner. Programming of the control electrical circuitry 114 can be affected via a user interface which can include a keypad, a computer terminal, a touchscreen, voice command, or other technique for inputting information.

During use in some operational situations, responsive to the one or more sensors 108 sensing the at least one characteristic associated with movement of the subject 106 or at least one physiological characteristic of the subject 106, the control electrical circuitry 114 directs the one or more actuators 110 to selectively constrict the flexible compression garment 102 (e.g., compress against the at least one body part 104) to provide more support thereto or to improve muscle or joint functioning, such as increased blood flow or increased oxygenation to at least one muscle or at least one joint of the at least one body part 104. For example, responsive to the one or more sensors 108 sensing the at least one characteristic associated with movement of the subject 106 or at least one physiological characteristic of the subject 106 is above (or below) a threshold level, the control electrical circuitry 114 directs the one or more actuators 110 to selectively constrict the flexible compression garment 102. In an embodiment, the constriction applied by the one or more actuators 110 can be a gradient of constriction, such as along the at least one body part 104. In a more specific embodiment, the control electrical circuitry 114 can direct the one or more actuators 110 to cause the flexible compression garment 102 to selectively constrict against at least one first portion of the at least one body part 104 with a first level or amount of constriction and selectively constrict at least one second portion of the at least one body part 104 with a second level of constriction that is different than the first level of constriction. As another example, the constriction applied by the one or more actuators 110 can include one or more constriction pulses. The constriction pulses can be applied substantially in rhythm, concert, or cycle with the sensed at least one characteristic of the subject 106, such as with a gait, pulse, respiration rate, blood pressure, strain, tension, or any other transitory sensed characteristic of the subject 106.

During use in other operational situations, responsive to the one or more sensors 108 sensing the at least one characteristic associated with movement of the subject 106 or at least one physiological characteristic of the subject 106, such as those related to a muscle activity or joint activity, the control electrical circuitry 114 directs the one or more actuators 110 to selectively dilate (e.g., relieve compression against the at least one body part 104) the flexible compression garment 102, such as during a portion of an athletic activity in which at least one muscle or the at least one joint of subject is minimally exerted or stressed, respectively. For example, responsive to the one or more sensors 108 sensing the at least one characteristic associated with movement of the subject or at least one physiological characteristic of the subject 106 that is below (or above) a threshold level, the control electrical circuitry 114 directs the one or more actuators 110 to selectively dilate the flexible compression garment 102. The selective dilation can include a gradient of dilation or a pulse of dilation similar or identical to the gradient and pulse constrictions described above.

In an embodiment, the threshold level discussed above includes one or more of an acceleration threshold level of the subject 106, a pulse threshold level of the subject 106, a time threshold level (e.g., duration of movement or exercise), an oxygen threshold level of the subject 106 (e.g., blood oxygen content), a chemical threshold level of a subject 106, a physiological threshold level of a subject 106 (e.g., a pressure, load, tension, torque, etc. applied by or on the subject 106 or a body part of the subject 106), a travel distance (e.g., movement distance or equivalent of distance travelled if on a stationary motion-conducive equipment) threshold level, an equipment use threshold level for the subject (e.g., number of steps taken on a treadmill, number of revolutions of a crank on a cycle, number of hits with a bat or club) or a temperature threshold level of the subject 106.

During use in operational situations, responsive to the one or more sensors 108 sensing the at least one characteristic associated with movement of the subject or at least one physiological characteristic of the subject 106, the control electrical circuitry 114 can direct the one or more actuators 110 to selectively constrict and selectively dilate, such as in a pulsatile pattern, cycle or rhythm, constrict for a duration and then dilate upon expiration of the duration, selectively constrict or selectively dilate different portions of the flexible compression garment 102, or selectively constrict or selectively dilate portions of the flexible compression garment 102 in a travelling gradient (e.g., creating peristaltic motion or a massage effect on the at least one body part 104).

For example, the control electrical circuitry 114 can direct the one or more actuators 110 to selectively constrict or selectively dilate the flexible compression garment 102 about the at least one body part 104 to a first selected amount, followed by selectively constricting or selectively dilating the flexible compression garment 102 to a second selected amount that is different than the first amount. In an embodiment, responsive to receiving the one or more sensing signals 109 from the one or more sensors 108 during selective constriction or dilation, the control electrical circuitry 114 can be configured to alter the actuation of the one or more actuators 110. For example, the control electrical circuitry 114 can direct the power supply 118 to alter (e.g., increase or decrease) an actuation stimulus supplied to the one or more actuators 110, thereby increasing or decreasing the selective constriction or dilation of the flexible compression garment 102 during use at least partially based on the one or more sensing signals 109 from the one or more sensors 108 sensed during selective compression or selective dilation. In an embodiment, an operational program or the control electrical circuitry 114 can include instructions for one or more of a plurality of amounts (e.g., strength) of constriction or dilation, one or more durations for each of the plurality of amounts, or discrete portions or locations of the flexible compression garment 102 at which the plurality of amounts can be applied.

In an embodiment, the garment system 100 can also be operated according to a feedback loop. For example, the control electrical circuitry 114 can direct the power supply 118 to alter (e.g., increase or decrease) an actuation stimulus supplied to the one or more actuators 110, thereby increasing or decreasing the selective constriction or dilation of the flexible compression garment 102 to a first level during use at least partially based on the one or more sensing signals 109 from the one or more sensors 108 sensed during selective compression or selective dilation, followed by the control electrical circuitry 114 again directing the power supply 118 to alter (e.g., increase or decrease) an actuation stimulus supplied to the one or more actuators 110, thereby increasing or decreasing the selective constriction or dilation of the flexible compression garment 102 to a different, second level during use at least partially based on updated information encoded in the one or more sensing signals 109 from the one or more sensors 108 sensed during selective compression or selective dilation.

Although only one flexible compression garment 102 is shown in FIG. 1A, in other embodiments, a plurality of flexible compression garments 102 can be worn on different body parts of the subject 106. In such an embodiment, each of the plurality of flexible compression garments 102 includes its own one or more actuators that can be individually operably coupled to the control system 112 and independently operate according to directions (e.g., actuation signals 116) from the control system 112. In an embodiment, each of the plurality of flexible compression garments 102 can include one or more sensors therein. In an embodiment, each of the plurality of flexible compression garments 102 can be controlled responsive to sensing signals from one or more sensors in a single portion of the motion-conducive equipment 103 (e.g., on a tread deck, handle, etc.) or each via a separate sensor(s) deployed on one or more portions of the motion-conducive equipment 103 (e.g., one in the tread deck and one in the handle).

In an embodiment, the at least one flexible compression garment 102 can include one or more sensors 108 therein. For example, a sensor 108 can be any of the sensors 108 described herein and configured to determine if the flexible compression garment is worn by a subject. For example, a muscle oxygenation sensor or thermal sensor can detect a reading in the normal range of human muscle oxygenation or skin temperature and thereby indicate that the flexible compression garment is worn by the subject. Any of the flexible compression garments herein can be controlled at least in part by the one or more sensors 108 disposed in or on the flexible compression garment 102. For example, a garment system herein or any portion thereof can be configured to remain inactive until a signal is received from one or more sensors 108 in a flexible compression garment 102 indicating that a subject is wearing the flexible compression garment 102. In an embodiment, multiple sensors 108 can be positioned in or on the flexible compression garment 103, whereby the control system of the garment system is configured to receive a signal from each sensor 108

As mentioned above, the one or more sensors 108 can be configured to sense at least one characteristic associated with movement of the subject or at least one physiological characteristic of the subject. For example, the at least one characteristic can be at least one physical characteristic, at least one chemical characteristic (e.g., biochemical or biological), or at least one physiological characteristic of the subject 106, such as of the at least one body part 104 or other body part of the subject 106 For example, the at least one characteristic can include at least one of a change in motion of travel of the subject 106 (e.g., a change in direction of travel of the subject 106, a change in velocity of the subject 106, or a change in acceleration of the subject 106), a load applied to the one or more sensors by a body part of the subject 106, pressure applied to the one or more sensors by a body part of the subject 106, tension applied to the one or more sensors by a body part of the subject 106, torque applied to the one or more sensors by a body part of the subject 106, a load on a body part of the subject, pressure on a body part of the subject 106, tension on a body part of the subject 106, pulse in a body part of the subject 106, velocity of at least a body part of the subject 106 (e.g., a leg of or the entire subject 106), acceleration of at least a body part of the subject 106 (e.g., an arm or the entire subject 106), velocity of at least a portion of the motion motion-conducive equipment 103, acceleration of at least a portion of the motion-conducive equipment 103, location of the subject 106, gait of the subject 106, pace at which the subject 106 moves, distance that the subject 106 has traveled, or variations or patterns of any of the foregoing. The at least one characteristic can include nerve activity of the subject 106, chemical excretion of the subject 106, temperature in a body part of the subject 106, heart rate of the subject 106, pulse in a body part of the subject 106, temperature of the ambient environment of the subject 106, oxygenation of a body part of the subject 106, acoustic emission from at least one joint or muscle of the subject 106, or other suitable characteristic that can be correlated with the subject 106, such as at one or more body parts of the subject 106. In an embodiment, the one or more sensors 108 are configured to only sense the at least one characteristic of at least one muscle of the subject 106, while in other embodiments, the one or more sensors 108 are configured to only sense the at least one characteristic of at least one joint of the subject 106.

In order to sense the at least one characteristic associated with movement of the subject 106 or at least one physiological characteristic of the subject 106, various sensors can be used. For example, in any of the embodiments disclosed herein, the one or more sensors 108 can include at least one of an electromyography sensor, a thermal or temperature sensor (e.g., a thermometer or infrared heat sensor), a muscle oxygenation sensor, an acoustic sensor, an accelerometer, a pedometer, a counter, a tension sensor, a pressure sensor, a torque sensor, a time keeper (e.g., watch, stop-watch, or timer), a pulse sensor, heart rate sensor, an oximeter, a global positioning system ("GPS") receiver, a revolution counter, an altimeter, a resistance meter, a voltage meter (e.g., multimeter), a chemical sensor, a biochemical sensor, a moisture sensor (e.g., for measuring perspiration), a hydration sensor (e.g., for measuring hydration levels in the subject), or a biosensor.

In some embodiments, the one or more sensors 108 can be integrally formed or incorporated in the motion-conducive equipment 103 or permanently affixed or secured to the motion-conducive equipment 103. In an embodiment, the one or more sensors 108 can be or removably affixed or secured to the motion-conducive equipment 103 as an additional or non-proprietary addition to the motion-conducive equipment 103 (e.g., the one or more sensors 108 can be removably affixed to and used on any piece of motion-conducive equipment 103). For example, the one or more sensors 108 can be affixed to a portion of the motion-conducive equipment 103 via a wrap, clip, tape, magnet, or band bearing the one or more sensors 108. The one or more sensors 108 can be disposed at least partially on an exterior surface of the motion-conducive equipment 103 (e.g., on a handle or pedal)—where the exterior surface defines a space that receives a body part such as a hand or foot during the movement—or is at least partially embedded in the motion-conducive equipment 103. In an embodiment, the one or more sensor 108 can be positioned on an interior portion of the motion-conducive equipment 103. For example, the interior portion can be configured to isolate the one or more sensors 108 from external contact, such as contact with the skin of the subject 106. For example, one or more pressure sensors can be positioned on an the interior portion of the running surface (e.g., tread deck or axle) of a treadmill, such that the one or more pressure sensors do not come in contact with the subject 106 but are able to sense the pressure applied by each footfall during movement thereon. In a more specific example, one or more pressure sensors can be positioned on each side of the tread deck of the treadmill, such that the one or more pressure sensors can detect differences in gait, stride, pace, or speed by sensing patterns or differences in the pressure applied by the left and right feet individually or collectively. The sensing signals can be used to infer, predict, or demonstrate a selected condition or state of the subject. Similar uses can include one or more sensors 108 in individual pedals on the motion-conducive equipment 103 or individual handles on the motion-conducive equipment 103. Patterns and differences in at least one characteristic can also be determined by comparing the differences in sensing signals at one or more of the sensors 108, 108', or 108" disposed on different portions of the motion-conducive equipment 103. For example, an imbalance in or inconsistent force exerted on handles of the motion-conducive equipment as compared to balanced or consistent force exerted on the tread deck of the motion-conducive equipment 103 can signal, infer, or demonstrate that a subject is favoring one side, favoring one leg, favoring one arm, or any of the above may be injured. As a further example, an increase in the force exerted on one or sensors 108 in the handles of a treadmill, stair climber, or elliptical trainer, as compared to the force exerted on the one or more sensors 108 in tread deck thereof, can demonstrate that a subject's legs or lungs are tiring or nearing a threshold level.

In an embodiment, the one or more sensors 108 are configured to sense onset of or a threshold level of activity or exertion, such as a threshold level of the at least one characteristic. In such an embodiment, the control electrical circuitry 114 is configured to direct the one or more actuators 110 to selectively constrict or dilate the flexible compression garment 102 responsive to the one or more sensors 108 sensing participation in the selected activity or the threshold level of exertion therein. In an embodiment, the control electrical circuitry 114 can direct the one or more actuators 110 to selectively constrict or selectively dilate the flexible compression garment 102 according to an operational program associated with the at least one characteristic associated with movement of the subject or at least one physiological characteristic of the subject, a selected profile, or a selected activity correlated to the at least one characteristic. One suitable sensor configured to sense nerve impulses of the at least one muscle indicative of the onset of the muscle activity includes one or more electromyography sensors, which can be attached, adhered, or embedded within or the motion-conducive equipment 103 or attached directly to the subject 106. For example, responsive to sensing the onset of muscle activity via the one or more electromyography sensors, the control electrical circuitry 114 can direct the one or more actuators 110 to cause the flexible compression garment 102 to selectively constrict. Examples of suitable electromyography sensors that can be used to practice one or more embodiments disclosed herein are disclosed in U.S. Patent Application Publication Nos. 20060058694 and 20130041235, and in Kim, et al., Science 333, 838-843 (2011), the disclosure of each of which is incorporated herein, in its entirety, by this reference.

In an embodiment, the one or more sensors 108 are configured to sense an injury of the subject 106. For example, the one or more sensors 108 can detect a level or change in one or more of a pace of the subject 106, gait of the subject 106, pulse of the subject 106, load or force applied by or on a body part, tension on or applied by a body part, torque applied by or on a body part, or strain on a body part inconsistent with an established level for that specific characteristic. The control system 112 can infer an injury, tiring, or an atypical condition based on such sensor signals. As another example, the one or more sensors 108 can detect a limp in the subject 106, or that the subject 106 is favoring a foot, leg, or arm, such as by comparing current sensing data with baseline or model sensing data for the same at least one characteristic. As yet another example, the one or more sensors 108 can detect an oxygen content, lactic acid content, hydration level, or other characteristic associated with an injury or cause of impaired performance.

In an embodiment, the one or more sensors 108 can include one or more passive infrared thermal sensors. For example, each passive infrared thermal sensor is positioned on or in the motion-conducive equipment 103 and configured to sense infrared radiation from the subject 106 or a body part of the subject 106, such as from the arm or hand of the subject 106 using the motion-conducive equipment 103. An increase in the infrared radiation can be indicative of or correlated with increased muscle temperature, which can be indicative of increased muscle activity. A decrease in the infrared radiation can be indicative of or correlated with decreased muscle temperature, which can be indicative of decreased muscle activity. For example, responsive to sensing an increase in or a threshold level of infrared radiation, the control electrical circuitry 114 can direct the one or more actuators 110 to cause the flexible compression garment 102 to selectively constrict or dilate. As another example, responsive to sensing a decrease in or less than a threshold level of infrared radiation, the control electrical circuitry 114 can direct the one or more actuators 110 to cause the flexible compression garment 102 to selectively constrict or selectively dilate due to muscle activity decreasing.

In an embodiment, the one or more sensors 108 can be at least one thermal sensor configured to sense the temperature of the ambient environment of the subject, temperature of the subject, or the temperature of a body part of the subject either directly or indirectly. In an embodiment, the flexible compression garment 102 can include one or more fluid channels through which coolant or heating fluid can flow, a fluid reservoir holding the coolant or heating fluid, and a pump configured to pump the fluid coolant or heating fluid from the reservoir through the one or more fluid channels. Thus, in such an embodiment, the control electrical circuitry 114 can direct the pump to pump fluid coolant or heating fluid from the fluid coolant reservoir through the one or more fluid channels to help cool or heat the subject 106 or the at least one body part of the subject 106.

In an embodiment, the one more sensors 108 can include one or more muscle oxygenation sensors or an oximeter. For example, each muscle oxygenation sensor can include a near infrared sensor positioned and configured to deliver light in the near infrared spectrum to at least one muscle of the subject 106 and detect light reflected from the at least one muscle (e.g., tissue), thereby sensing absorption of the near infrared light by the muscle that differs in oxygenated and deoxygenated tissues. Examples of near infrared sensors for measuring the oxygenation of muscle tissues that can be used to practice one or more embodiments disclosed herein are disclosed in in Hamaoka, et al., Phil. Trans. R. Soc. A (2011) 369, 4591-4604, which is incorporated herein, in its entirety, by reference. Changes in the absorption of near infrared light from the at least one muscle can be correlated with or can be indicative of increased or decreased muscle oxygenation. For example, changes in the absorption of the near infrared light can be associated with increased exertion or decreased muscle oxygenation (e.g., associated with overwork, cramping, claudication, or other impaired performance).

In an embodiment, responsive to sensing a change in muscle oxygenation, the control electrical circuitry 114 can direct the one or more actuators 110 to cause the flexible compression garment 102 to selectively constrict or selectively dilate. For example, responsive to sensing an increase in muscle oxygenation over a threshold level, the control electrical circuitry 114 can direct the one or more actuators 110 to cause the flexible compression garment 102 to selectively constrict to thereby increase compression of the flexible compression garment 102 against the at least one body part 104 due to muscle activity increasing. For example, responsive to sensing a decrease in muscle oxygenation below a threshold level, the control electrical circuitry 114 can direct the one or more actuators 110 to cause the flexible compression garment 102 to selectively dilate to thereby relieve compression against the at least one body part 104 due to muscle activity decreasing. In other embodiments, the one or more oxygenation sensors can be used to sense a change in joint oxygenation.

In an embodiment, the one or more sensors 108 can include multiple near infrared source-detector pairs that can measure spatial and regional differences in skeletal muscle oxygenation or localized changes in the subject 106. For example, responsive to sensing a localized decrease in infrared radiation below a threshold level indicative of significantly decreased muscle oxygenation and blood flow associated with a muscle cramp, the control electrical circuitry 114 can direct the one or more actuators 110 to cause the flexible compression garment 102 to selectively constrict to provide localized support and increase blood pressure. For example, responsive to sensing a varied decrease in infrared radiation indicative of a gradient of decreased muscle oxygenation and blood flow associated with muscle overexertion, the control electrical circuitry 114 can direct the one or more actuators 110 to cause the flexible compression garment 102 to selectively constrict with a first level of compression and selectively constrict with a second level of compression or to cause the flexible compression garment 102 to intermittently selectively constrict against only a part of the at least one body part 104 to provide localized to increased blood flow to part of the at least one body part 104.

In an embodiment, the one more sensors 108 can include one or more acoustic transducers configured to irradiate the one or more body parts with acoustic radiation and receive reflected acoustic radiation responsive thereto. The received reflected acoustic radiation can be correlated with or can be indicative of muscle activity or joint activity of one or more body parts including the at least one body part 104. For example, a relatively stronger/more intense reflected acoustic radiation received by the one or more acoustic transducers can be indicative of relatively tenser, more active muscles, while a relatively weaker/less intense reflected acoustic radiation received by the one or more acoustic transducers can be indicative of relatively looser, less active muscles.

In an embodiment, the acoustic transducer includes an ultrasound transducer, and each of the acoustic radiation and the reflected acoustic radiation includes ultrasound radiation. The received reflected ultrasound radiation can be correlated with or can be indicative of at least one characteristic of one or more body parts including the at least one body part 104. For example, altered echogenicity detected by the one or more acoustic transducers can be indicative of swelling or inflammation of the muscle. For example, altered echogenicity detected by the one or more acoustic transducers can be indicative of joint effusion of the at least one joint. For example, Doppler ultrasound sensing of the at least one muscle can detect increased blood flow within the at least one muscle, indicating increased activity of the at least one muscle. For example, Doppler ultrasound sensing of a ligament or tendon can detect limited activity within the ligament or tendon, indicating stress to the region. In an embodiment, responsive to the one or more acoustic transducers detecting a change in at least one characteristic of the at least one body part, the control electrical circuitry 114 can direct the one or more actuators 110 to cause the flexible compression garment 102 to selectively constrict or selectively dilate around at least one muscle or at least one joint. For example, responsive to sensing echogenicity indicating an increase in muscle or joint activity, the control electrical circuitry 114 can direct the one or more actuators 110 to cause the flexible compression garment 102 to selectively constrict around at least one muscle or at least one joint of the at least one body part 104. For example, responsive to sensing echogenicity indicating a decrease in muscle or joint activity, the control electrical circuitry 114 can direct the one or more actuators 110 to cause the flexible compression garment 102 to selectively dilate around the at least one muscle or at least one joint of the at least one body part 104 due to muscle activity decreasing. For example, responsive to sensing echogenicity indicating inflammation in the least one muscle or the at least one joint, the control electrical circuitry 114 can direct the one or more actuators 110 to cause the flexible compression garment 102 to selectively constrict, and thereby support, the at least one muscle or at least one joint of the at least one body part 104.

In an embodiment, the one more sensors 108 can include one or more acoustic myography sensors positioned and configured to sense acoustic emission from a body part, such as the at least one body part 104. An example of an acoustic myography sensor for sensing muscle use suitable for practicing one or more embodiments disclosed herein is disclosed in Harrison, et al., Physiol Rep, 1(2): e00029; 2013, the disclosure of which is incorporated herein, in its entirety, by this reference. For example, responsive to sensing a high frequency by the acoustic myography sensor, indicative of increased muscle use, the control electrical circuitry 114 can direct the one or more actuators 110 to cause the flexible compression garment 102 to selectively constrict around at least one muscle of the at least one body part 104.

In an embodiment, the one more sensors 108 can include one or more acoustic sensors positioned and configured to sense acoustic emission from at least one joint. For example, the one or more acoustic sensors can be positioned adjacent to or proximate to at least one joint (e.g., an ankle near the pedal as illustrated in FIG. 1A, a wrist, or a knee) so that the one or more acoustic sensors can receive acoustic emission from the at least one joint that can be indicative of joint problems, such as aggravation of an arthritic or an osteoarthritic condition and resultant arthralgia. For example, responsive to sensing acoustic emission or an increase in acoustic emission from the at least one joint, the control electrical circuitry 114 can direct the one or more actuators 110 to cause the flexible compression garment 102 to selectively constrict near or around the at least one joint and the at least one muscle around the at least one joint of the at least one body part 104 to thereby alleviate arthralgia.

In an embodiment, the one more sensors 108 can include one or more of at least one chemical sensor, at least one biochemical sensor, or at least one biosensor configured to detect an analyte from the skin (e.g., through the hands), a muscle, or a joint of the of the subject 106. For example, at least one chemical sensor, at least one biochemical sensor, or at least one biosensor can be configured to detect at least one of an ion, a salt, glucose, a lactate, lactic acid, or an inflammatory molecule from the skin, at least one muscle, or the at least one joint of the subject 106. For example, responsive to sensing an increase in lactic acid in at least one muscle by a biosensor indicative of muscle fatigue, the control electrical circuitry 114 can direct the one or more actuators 110 to cause the flexible compression garment 102 to selectively constrict around the at least one muscle of the subject 106. In an embodiment, a chemical sensor can detect the level of salt in sweat from a subject. For example, the amount of salt in the sweat of a subject 106 indicates possible hypernatremia (e.g., dehydration) or hyponatremia and the symptoms thereof, including imminent cramping. For example, responsive to sensing an undesirable salt level in the sweat of a subject 106 being indicative of hypernatremia, the control electrical circuitry 114 can direct the one or more actuators 110 to cause the flexible compression garment 102 to selectively constrict around at least one body part 104 of the subject 106.

In an embodiment, the one more sensors 108 can include one or more accelerometers positioned and configured to sense acceleration or deceleration of a subject 106 or body part of the subject 106, such as the at least one body part 104 or at least an additional body part. For example, responsive to sensing a high deceleration rate by the accelerometer, the control electrical circuitry 114 can direct the one or more actuators 110 to cause the flexible compression garment 102 to selectively constrict, such as around at least one muscle of the at least one body part 104 to brace the muscle against forces on the at least one body part 104 during deceleration. In another example, responsive to sensing a high acceleration rate by the accelerometer, the control electrical circuitry 114 can direct the one or more actuators 110 to cause the flexible compression garment 102 to selectively dilate, such as around at least one muscle or joint of the at least one body part 104 to provide freedom of movement to the at least one muscle or joint of at least one body part 104 during acceleration.

In an embodiment, the one more sensors 108 can include at least one of one or more counters (e.g., a pedometer) positioned and configured to count a specific incidence of physical activity or movement of the subject 106 or body part of the subject 106 (e.g., footsteps, pedal rotation cycle, arm movement, laps, etc.), such as the at least one body part 104 or at least an additional body part. For example, responsive to sensing a specific number of footfalls or strides with a pedometer, the control electrical circuitry 114 can direct the one or more actuators 110 to cause the flexible compression garment 102 to selectively constrict, such as around at least one muscle of the at least one body part 104 to support the at least one muscle. In another example, responsive to sensing a specific number of footfalls on a pedometer, the control electrical circuitry 114 can direct the one or more actuators 110 to cause the flexible compression garment 102 to selectively dilate, such as around at least one muscle of the at least one body part 104 to allow more blood flow to the at least one muscle. In an embodiment, responsive to a specific number of counts, such as steps, the control electrical circuitry 114 can direct the one or more actuators 110 to cause the flexible compression garment 102 to selectively constrict or selectively dilate in increasing or decreasing amounts as the count increases; in a gradient, such as along the at least one body part 104; or in a pulsatile manner substantially as described herein.

In an embodiment, the one more sensors 108 can include one or more tension sensors (e.g., a strain gauge, a force transducer, or a universal-force moment sensor) configured to detect or measure tension applied by or on a body part of the subject 106, such as one or more muscles, tendons, or ligaments. For example, responsive to receiving sensing data of tension beyond a threshold level on at least one body part 104 or at least an additional body part of a subject 106, the control electrical circuitry 114 can direct the one or more actuators 110 to cause the flexible compression garment 102 to selectively constrict, such as around an ankle or leg, to support the ankle or restrict the movement thereof. For example, responsive to receiving sensing data of tension below a threshold level on a body part of a subject 106, the control electrical circuitry 114 can direct the one or more actuators 110 to cause the flexible compression garment 102 to selectively dilate, such as around the at least one body part 104 to allow more blood flow or freedom of movement thereto. In an embodiment, responsive to the one or more sensors 108 detecting a tension of a body part, the control electrical circuitry 114 can direct the one or more actuators 110 to cause the flexible compression garment 102 to selectively constrict or selectively dilate in a gradient, such as along the at least one body part 104, or in a pulsatile manner substantially as described herein.

In an embodiment, the one more sensors 108 can include one or more pressure sensors (e.g., a piezoelectric sensor or strain gauge, a force or pressure transducer, a capacitive pressure sensor, or an electromagnetic pressure sensor) configured to detect pressure, load, or force applied by or on a body part of the subject 106 (e.g., at a foot, joint, or muscle), such as the at least one body part 104 or at least an additional body part. For example, responsive to receiving sensing data of pressure or force beyond a threshold level on the at least one body part 104 or at least an additional body part of a subject 106, the control electrical circuitry 114 can direct the one or more actuators 110 to cause the flexible compression garment 102 to selectively constrict, such as around an ankle or leg, to provide support or restrict the movement thereof. In an embodiment, strain and pressure sensors can be used over time to sense pressure or tension in the at least one body part 104 or at least an additional body part as a function of time. Both strain and pressure sensors can also be used to determine number of steps/distance traveled by the subject 106 and adjust the selective amount of constriction or dilation of the flexible compression garment 102, as desired.

For example, responsive to receiving sensing data of pressure or force below a threshold level on a body part of a subject 106, the control electrical circuitry 114 can direct the one or more actuators 110 to cause the flexible compression garment 102 to selectively dilate, such as around the at least one body part 104 to allow more blood flow or freedom of movement thereto. In an embodiment, responsive to the one or more sensors 108 detecting pressure or force on a body part, the control electrical circuitry 114 can direct the one or more actuators 110 to cause the flexible compression garment 102 to selectively constrict or selectively dilate in a gradient, such as along the at least one body part 104, or in a pulsatile manner substantially as described herein.

In an embodiment, the one or more sensors can include one or more torque sensors or torque transducers configured to detect the amount of torque applied by the subject 106. By way of non-limiting example, a torque sensor can be positioned on a rotating portion of the motion-conducive equipment 103, such as the crank of a cycle, or the pulley or flywheel of a rowing machine. For example, responsive to receiving sensing data of torque or force beyond a threshold level applied by or on at least one body part 104 of a subject 106, the control electrical circuitry 114 can direct the one or more actuators 110 to cause the flexible compression garment 102 to selectively constrict, such as around an ankle, arm, or leg, to provide support or restrict the movement thereof. In an embodiment, torque sensors can be used over time to sense torque exerted by or on the at least one body part 104 as a function of time. Torque can also be used to determine number of discrete motions, steps, or distance traveled by the subject 106 and adjust the selective amount of constriction or dilation of the flexible compression garment 102, as desired.

For example, responsive to receiving sensing data of pressure or force below a threshold level on a body part of a subject 106, the control electrical circuitry 114 can direct the one or more actuators 110 to cause the flexible compression garment 102 to selectively dilate, such as around the at least one body part 104 to allow more blood flow or freedom of movement thereto. In an embodiment, responsive to the one or more sensors 108 detecting pressure or force on a body part, the control electrical circuitry 114 can direct the one or more actuators 110 to cause the flexible compression garment 102 to selectively constrict or selectively dilate in a gradient, such as along the at least one body part 104, or in a pulsatile manner substantially as described herein.

In an embodiment, the one more sensors 108 can include one or more time-keepers configured to detect the duration of an activity or duration of use of a body exertion of a body part, such as the at least one body part 104 or at least an additional body part. For example, responsive to passage of a specific duration of time, the control electrical circuitry 114 can direct the one or more actuators 110 to cause the flexible compression garment 102 to selectively constrict, to provide resistance or support, or restrict the movement thereof. For example, responsive to passage of a specific duration of time, the control electrical circuitry 114 can direct the one or more actuators 110 to cause the flexible compression garment 102 to selectively dilate, such as around the at least one body part 104 to allow more blood flow or freedom of movement thereto. In an embodiment, responsive to the passage of a specific duration of time, the control electrical circuitry 114 can direct the one or more actuators 110 to cause the flexible compression garment 102 to selectively constrict or selectively dilate in a gradient, such as along the at least one body part 104, or in a pulsatile manner substantially as described herein.

In an embodiment, the one more sensors 108 can include a global positioning system ("GPS") receiver or an altimeter configured to detect a distance traveled, velocity of the subject 106 or a body part of the subject 106, or an elevation of the subject 106. For example, responsive to sensing a specific distance travelled or elevation at which the selected activity is taking place, the control electrical circuitry 114 can direct the one or more actuators 110 to cause the flexible compression garment 102 to selectively constrict, to provide resistance or support, or restrict the movement thereof. As an example, responsive to sensing a specific distance travelled or elevation at which the selected activity is taking place, the control electrical circuitry 114 can direct the one or more actuators 110 to cause the flexible compression garment 102 to selectively dilate, such as around the at least one body part 104 to allow more blood flow or freedom of movement thereto. In an embodiment, responsive to detecting a specific distance travelled or elevation at which the specific activity is taking place, the control electrical circuitry 114 can direct the one or more actuators 110 to cause the flexible compression garment 102 to selectively constrict or selectively dilate in a gradient, such as along the at least one body part 104, or in a pulsatile manner substantially as described herein.

In an embodiment, the one or more sensors 108 can include a revolution counter configured to count the revolutions of a part of the motion-conducive equipment. The number of revolutions of a piece of motion-conducive equipment can be used to determine the distance traveled by a subject using the piece of motion-conducive equipment. For example, the number of revolutions of a wheel on a stationary exercise bicycle can be used to calculate the equivalent distance traveled by the subject during a workout. Responsive to sensing a specific distance travelled (or equivalent distance travelled), the control electrical circuitry 114 can direct the one or more actuators 110 to cause the flexible compression garment 102 to selectively constrict or selectively dilate.

In an embodiment, the one more sensors 108 can include one or more pulse sensors configured to measure a pulse in a body part of the subject 106 (e.g., a peripheral pulse in an artery in a foot, hand, or other body part). Thus, in an embodiment, the one or more pulse sensors can be selectively positioned on the motion-conducive equipment 103 or optionally in the flexible compression garment 102 to be proximate to an artery of the subject 106. For example, a pulse sensor can include an optical pulse sensor, such as those used in fitness bracelets, or an acoustic sensor. In an embodiment, responsive to sensing an increase in the peripheral pulse rate in the at least one body part 104 or at least an additional body part of the subject 106 indicative of increased muscle activity within the body part, the control electrical circuitry 114 can direct the one or more actuators 110 to cause the flexible compression garment 102 to selectively constrict around the at least one muscle or at least one joint of the at least one body part 104. As another example, responsive to sensing a decrease in the pulse rate in the at least one body part 104 or at least an additional body part of the subject 106 indicative of decreased muscle activity within the body part 104, the control electrical circuitry 114 can direct the one or more actuators 110 to cause the flexible compression garment 102 to dilate around at least one muscle or at least one joint of the at least one body part 104.

In an embodiment, one more optional additional types of sensors 108' can be incorporated onto the motion-conducive equipment 103 and operably coupled to the control electrical circuitry 114. Additionally or alternatively, the one or more additional sensors 108' can be worn on a wearable device that can be worn on any body part of the subject 106. In an embodiment, the one or more additional types of sensors can include one or more heart rate sensors that are configured to sense a heart rate of the subject 106 or one or more electrocardiography sensor. For example, the sensor 108' can include a chest band sensor that is incorporated into the wearable device worn around a torso and configured to sense heart rate or electrocardiographic activity. For example, the one or more sensors 108' can include a flexible low profile sensor that is embedded in the motion-conducive equipment 103 or wearable device and in direct or indirect contact with the torso, and is configured to sense heart rate or electrocardiographic activity. Examples of low profile, stretchable and flexible heart rate and electrocardiography sensors are described in U.S. Patent Application Publication Nos. 20060058694 and 20130041235, previously incorporated by reference. In an embodiment, the one or more heart rate sensors can include a pulse sensor for measuring a peripheral pulse, such as in a limb, as described above.

Responsive to sensing an increase in the heart rate of the subject 106 indicative of increased overall muscle activity, the control electrical circuitry 114 can direct the one or more actuators 110 to cause the flexible compression garment 102 to selectively constrict around at least one muscle or at least one joint of the at least one body part 104. As another example, responsive to sensing a decrease in the heart rate of the subject 106 indicative of decreased muscle activity, the control electrical circuitry 114 can direct the one or more actuators 110 to cause the flexible compression garment 102 to dilate around at least one muscle or at least one joint of the at least one body part 104.

By way of another example and having applicability to any of the sensors 108 or optional additional types of sensors 108' disclosed herein, in an embodiment, actuating the one or more actuators 110 to cause the flexible compression garment 102 to selectively constrict or selectively dilate is responsive to the at least one characteristic sensed by one or more sensors being indicative of the subject 106, or a body part of the subject 106, being injured or being strained past a strain limit. In another embodiment having applicability to any of the sensors 108 disclosed herein, actuating the one or more actuators 110 to cause the flexible compression garment 102 to selectively constrict or selectively dilate (e.g., apply or relieve compression against the at least one body part 104) is responsive to the at least one characteristic sensed by one or more sensors 108 being indicative of the at least one muscle being exerted. In another embodiment having applicability to any of the one or more sensors 108 disclosed herein, actuating the one or more actuators 110 to cause the flexible compression garment 102 to selectively constrict or selectively dilate can be responsive to the at least one characteristic sensed by the one or more sensors 108 being indicative of at least one muscle not being exerted beyond a threshold. For example, the one or more sensors 108 can indicate that at least one muscle is not being exerted at or near a physiological or functional limit thereof, and the flexible compression garment 102 adjusts the amount of constriction applied around the at least one muscle to cause the muscle to work harder, such as during strength training.

In an embodiment, one or more of any of the different types of sensors 108, 108', 108" described herein can be used in the same garment system 100, such as being disposed in the same motion-conducive equipment 103, wearable device, flexible compression garment 102, or more than one of the foregoing used simultaneously on the same or different body parts of the subject 106. For example, at least one pressure sensor and at least one accelerometer can be disposed in each of the tread decks (or foot rests) and handles of a rowing machine. During an activity, such as rowing, sensing data from the pressure sensors and the accelerometers in each tread deck and handle can be compared by the control electrical circuitry 114 to determine forces involved in the motion, a level of activity, a type of activity, an indication of a limp or other injury to the subject 106, duration of the activity, or any other detectable characteristics. A reduced pressure applied to one foot or change in accelerometer data for one limb of the subject 106 can indicate that the subject 106 is favoring a specific leg and therefore likely injured. Responsive to detection of a limp or favoring one or more body parts of the subject 106, the control electrical circuitry 114 can direct the one or more actuators 110 to selectively constrict around the limb or body part based on sensing data indicative of a limp in order to provide extra support.

As another example, responsive to detecting a specific type of motion or activity, such as running on a treadmill or cycling, the control electrical circuitry 114 can direct the one or more actuators 110 to selectively constrict, or selectively dilate to provide support, freedom of movement, increased blood flow, or resistance to the at least one body part 104 of the subject 106. In an embodiment, the one or more sensors 108 can include a GPS receiver or revolution counter and an accelerometer. The sensing data from the accelerometer and the distance traveled, as sensed by the GPS receiver or revolution counter (e.g., on a treadmill or exercise bicycle), can be correlated by the control electrical circuitry 114 to determine the gait, pace, or stride of the subject 106 during an activity. In an embodiment, the one or more sensors 108 can include a GPS receiver or revolution counter and a time-keeper, such as a watch. The distance traveled by the subject 106 over a specific time period, as measured by the timer, can be used to determine a pace of the subject 106 during the selected activity. The control electrical circuitry 114 can direct the one or more actuators 110 to selectively constrict or selectively dilate responsive to the detected gait or pace of the subject 106. Additionally, the control electrical circuitry 114 can use the detected gait or pace to determine if the subject 106 is participating in the selected activity or level of exertion in the selected activity.

A combination of the any of the different types of the one or more sensors 108, 108', or 108" disclosed herein can be used to determine participation by the subject 106 in a selected activity, the level of exertion of the subject in an activity, injury to the subject, or any at least one characteristic associated with movement of the subject or at least one physiological characteristic of the subject as described herein. Such a determination can be carried out by the control system 112, such as by the control electrical circuitry 114 therein.

In an embodiment, the one or more actuators 110 can selectively constrict or selectively dilate during movement of the subject 106, such as while the subject 106 is participating in the selected motion or activity. In an embodiment, the one or more actuators 110 can selectively constrict or selectively dilate only during inactivity of the subject 106. In an embodiment, the one or more actuators 110 can selectively constrict or selectively dilate without regard to movement, motion, or inactivity of the subject 106. In an embodiment, the control system 112 can be configured to automatically terminate operation of the one or more actuators 110 or motion-conducive equipment 103 responsive to one or more of the level of exertion of the subject in an activity, injury to the subject, or any at least one characteristic associated with movement of the subject or at least one physiological characteristic of the subject as described herein, such as at least one thereof being above or below a threshold level for safety as determined by the control electrical circuitry 114 or the subject.

The one or more actuators 110 can be selected from a number of suitable different types of actuators. Additionally, as will be discussed in more detail below, the one or more actuators 110 can be positioned in a number of different configurations. For example, in any of the embodiments disclosed herein, the one or more actuators 110 can include at least one of one or more electroactive polymer actuators, one or more electroactive metallic actuators, one or more thermally active polymer actuators, one or more motors, or one or more hydraulic actuators.

In an embodiment, the one or more electroactive polymer actuators include one or more actuator elements at least partially formed from ferroelectric polymers, dielectric elastomers, or electrostrictive graft elastomers. Responsive to a voltage or current applied by the power supply 118 based on instructions from the control electrical circuitry 114, the electroactive polymer actuators can increase or decrease in length, diameter, or other dimension depending on the polarity of the applied voltage to cause the flexible compression garment 102 to selectively constrict or dilate. For example, suitable electroactive polymers for the electroactive polymer actuators include at least one of NuSil CF19-2186 commercially available from NuSil Technology of Carpinteria, Calif., silicone elastomers, acrylic elastomers (e.g., VHB 4910 acrylic elastomer commercially available from 3M Corporation of St. Paul, Minn.), polyurethanes, thermoplastic elastomers, copolymers comprising polyvinylidene difluoride ("PVDF"), pressure-sensitive adhesives, fluoroelastomers, polymers comprising silicone and acrylic moieties, or other suitable electroactive polymers.

In an embodiment, the one or more electroactive metallic actuators include one or more actuator elements at least partially formed from a shape memory material. For example, the shape memory material can include a nickel-titanium shape memory alloy, such as nitinol or other suitable nickel-titanium alloy composition. Responsive to the power supply 118 passing a current through the shape memory material to heat the shape memory material based on instructions from the control electrical circuitry 114, the electroactive metallic actuators can increase or decrease in length, diameter, or other dimension depending on the temperature to which the shape memory material is heated to cause the flexible compression garment 102 to selectively constrict or dilate.

In an embodiment, the one or more thermally active polymer actuators can include one or more actuator elements at least partially formed from temperature-responsive polymers, such as polyester, polyurethane, polypropylene, polyethylene, nylon, or combinations thereof. Responsive to heat or change in temperature applied by the power supply 118 based on instructions from the control electrical circuitry 114, the thermally active polymer actuators can increase or decrease in length, diameter, or other dimension depending on the temperature change to cause the flexible compression garment 102 to selectively constrict or dilate. For example, suitable temperature responsive polymers for the thermally active polymer actuators include at least one of a polyester, a polyurethane, a polypropylene, a polyethylene (e.g., polytetrafluoroethylene), nylon, or other suitable temperature responsive polymers.

Examples of such nickel-titanium shape memory alloys are currently commercially available from Dynalloy, Inc. and sold under the trade name Flexinol®. Flexinol HT® has a transition temperature of about 194° F., with an activation start temperature at about 190° F. and an activation finish temperature at about 208° F. Such nickel-titanium alloys can gradually and controllably contract in length about 2% to about 5% of their length or other dimension as they are heated from the activation start temperature to the activation finish temperature.

In an embodiment, the one or more motors include one or more micro-electro-mechanical actuators. For example, the one or more micro-electro-mechanical motors can include one or more micro-piezoelectric actuators, one or more micro-electrostatic actuators, or one or more micro-electromagnetic actuators. Examples of suitable micro-electromechanical motors that can be used to practice one or more embodiments disclosed herein are disclosed in Acoust. Sci. & Tech. 31, 2 (2010), the disclosure of which is incorporated herein, in its entirety, by this reference. As another example, one suitable micro-piezoelectric actuator is New Scale's SQUIGGLE™ motor.

In an embodiment, the one or more actuators 110 include a gear system configured to constrict or dilate (e.g., tighten or loosen) the at least one flexible compression garment on the at least one body part of the subject. For example, the gear system can include a reel having gears therein and lacing connected therethrough. The gear system can be similar or identical to the Boa Closure System sold by Boa Technology, Inc. of Denver, Colo. or similar system. The gear system can be operably coupled to a motor configured to cause the gear system to tighten or loosen the lacing connected to the reel. The lacing of the gear system can extend circumferentially or longitudinally through the flexible compression garment 102. Responsive to receiving an actuation signal 116 from the control electrical circuitry 114, the motor of the gear system tightens or loosens the lacing therein, thereby constricting or dilating the flexible compression garment 102 circumferentially or longitudinally without manual manipulation.

In an embodiment, the one or more actuators 110 can include a compressed gas system configured selectively constrict or selectively dilate the flexible compression garment 102. The compressed gas system is configured to provide inflow of compressed gas into or outflow of the compressed gas from at least a portion of the at least one flexible compression garment 102. For example, the flexible compression garment 102 can include one or more discrete, air-tight, chambers extending circumferentially or longitudinally therethrough. Each of the discrete chambers being fluidly connected to a source of compressed gas, such as a compressed gas cylinder having a regulator connected thereto. In an embodiment, responsive to receiving the actuation signal from the control electrical circuitry, the compressed gas system can cause the regulator to allow inflow of gas from the cylinder into one or more of the discrete, air-tight chambers thereby constricting the flexible compression garment 102. In an embodiment, responsive to receiving the actuation signal from the control electrical circuitry, the compressed gas system can cause the regulator or valve connected to one or more of the discrete, air-tight chambers to open thereby dilating the flexible compression garment 102.

In an embodiment, at least one of the one or more sensors; one or more actuators; control electrical circuitry including any of the power source, control electrical circuitry, memory (not shown in FIG. 1A), or user interface (not shown in FIG. 1A) can include a waterproof construction or configuration within the at least one flexible compression garment, at least one wearable device, or at least one piece of motion-conducive equipment. For example, sweat produced during exercise can decrease or terminate proper functioning of electrical components, such as the control electrical circuitry, one or more sensors, or one or more actuators. In an embodiment, the control electrical circuitry or one or more actuators can be enclosed or positioned in a waterproof or watertight material, such as a plastic, to ensure water (e.g., sweat) does not interfere with the proper functioning of the garment system. The waterproof construction can include discrete waterproof portions (e.g., pockets, enclosures, or compartments) in the at least one flexible compression garment, at least one wearable device, or the at least piece of motion-conducive equipment. Such waterproof portions can be reusable or resealable.

Figure 1B:
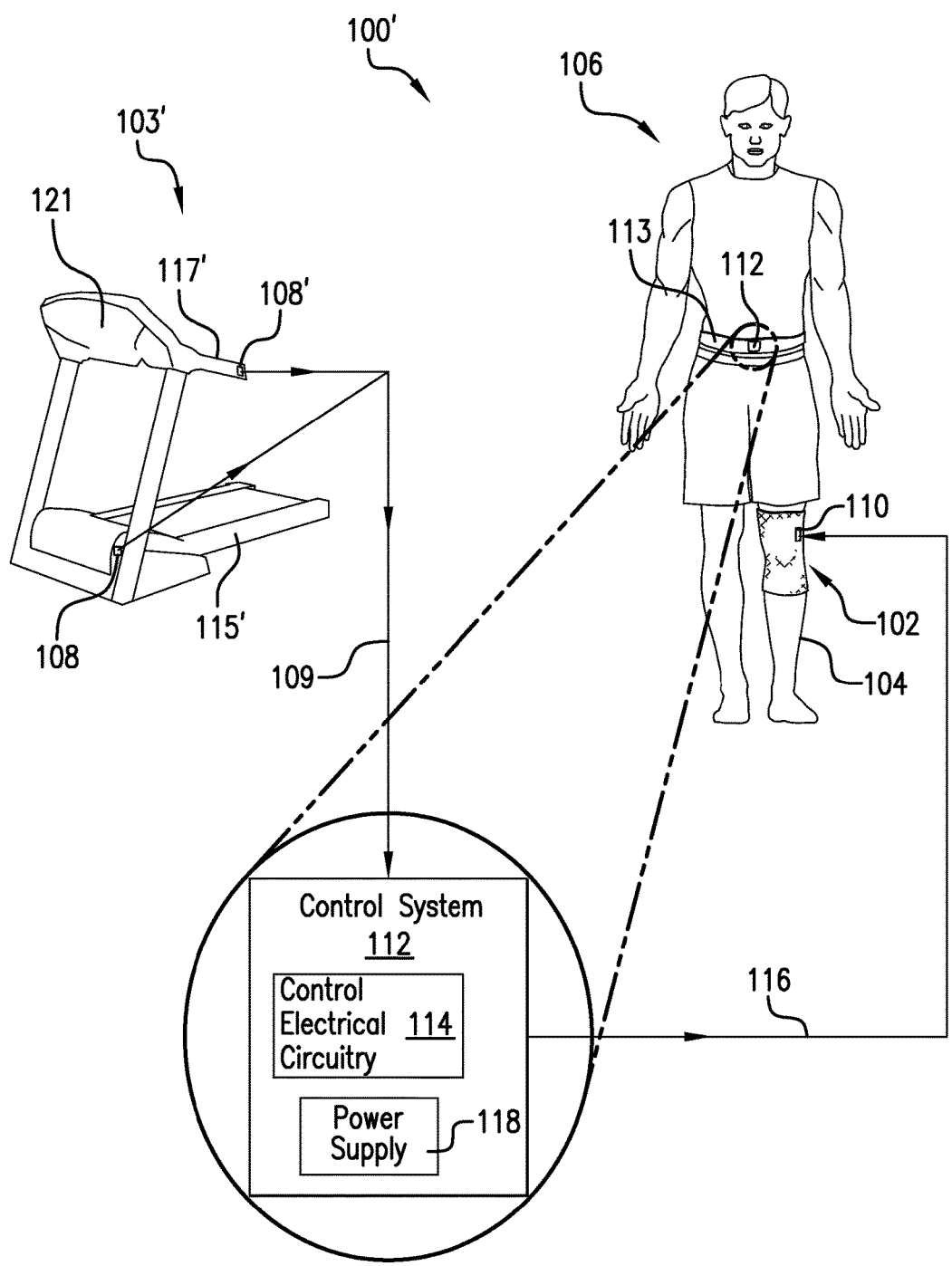
FIG. 1B is a diagrammatic view of a garment system according to an embodiment.

FIG. 1B is an illustration of a garment system 100', according to an embodiment. The garment system 100' is similar or identical to the garment system 100 depicted in FIG. 1A and described above, including all of the similarly numbered components therein. The garment system 100' includes the at least one flexible compression garment 102 worn on the at least one body part 104, as described herein. The garment system 100' can include motion-conducive equipment 103' in the form of a treadmill as shown. The treadmill includes a tread deck 115' for running on and a handle or support 117' for balance or support during motion or running. The treadmill can include one or more sensors 108, 108', or 108" thereon. For example, the one or more sensors 108 can be disposed on the tread deck 115' such as on an axle thereof, or one or more sensors 108' can be disposed on the handle 117'. The control system 112 can be disposed in a wearable device worn on the at least one body part 104 or an additional body part of the subject 106. In an embodiment, the control system 112 can be disposed on or in an equipment controller 121 of the motion-conducive equipment 103'. As discussed in more detail below, the equipment controller 121 can control one or more movement properties of the motion-conducive equipment 103'.

The term "wearable device" as used herein is not limited to devices that can be worn around a body part of the subject 106, but rather is intended to mean a device associated with the subject 106 so as to substantially remain on or associated with the subject 106 during movement thereof. In an embodiment, the wearable device 113 can be attached to the at least an additional body part by an attachment device. For example, the wearable device 113 can be configured as a patch, bandage, epidermal electronics, or the like, having an attachment device configured to connect to the subject 106. The attachment device can include one or more of an adhesive, hook and loop material, clips, or other suitable means. The wearable device 113 can be configured to be associated with a user by inserting the wearable device 113 between one or more layers of clothing or a layer of clothing and the skin (e.g., inserted inside of a sock, shoe, or shirt).

In an embodiment, at least one of the one or more sensors 108, 108', or 108" can be removably or reusably attached to or positioned on at least one of any motion-conducive equipment 103, wearable device 113, or flexible compression garment 102.

Figure 2A:
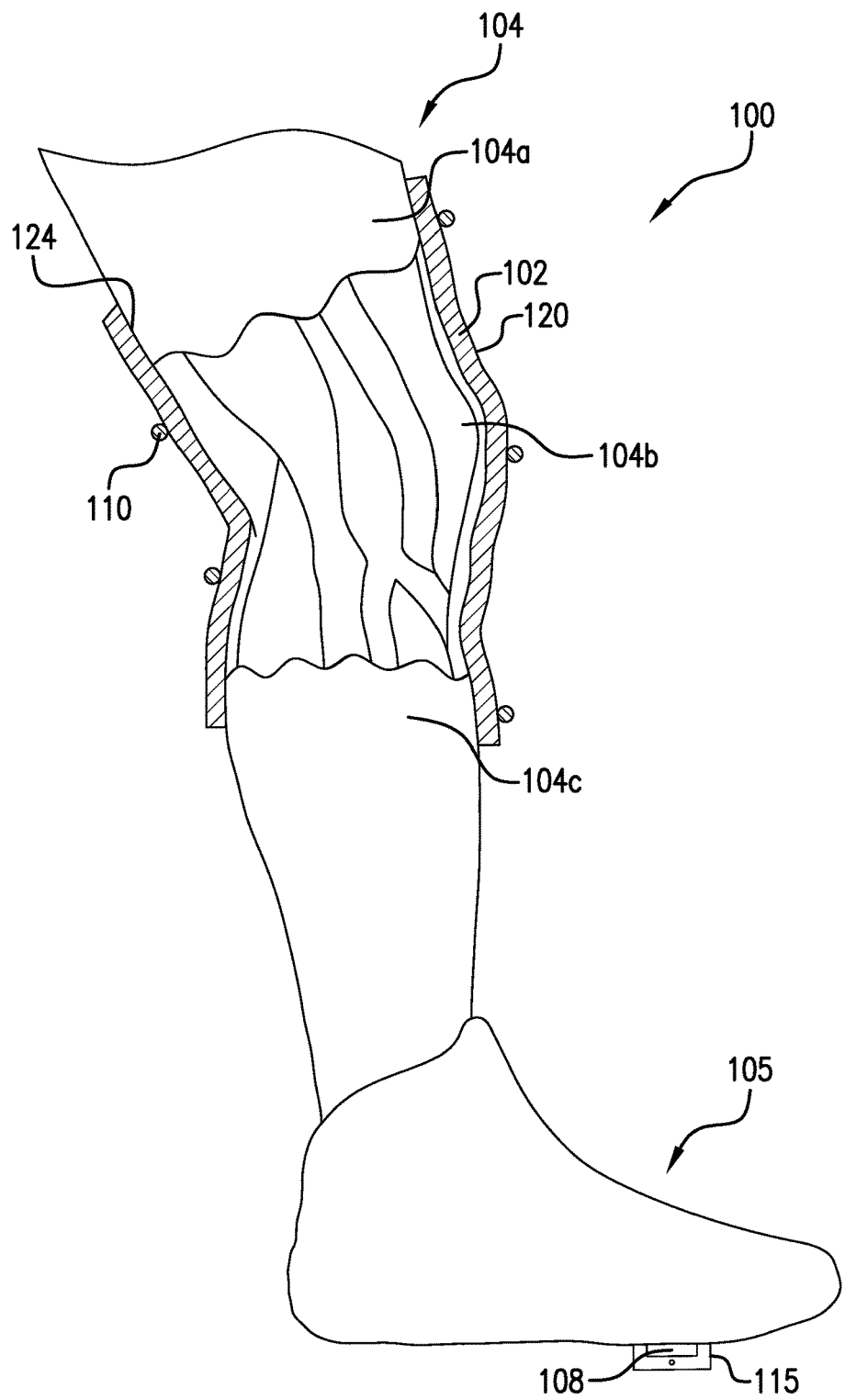
FIG. 2A is a side cutaway view of an embodiment of a garment system including a flexible compression garment worn on a leg of a subject and a portion of motion-conducive equipment in contact with the subject.

FIG. 2A is a side cutaway view of an embodiment of the flexible compression garment 102 of the garment system shown in FIG. 1A, which is worn on the at least one body part 104 of the subject 106, according to an embodiment. FIG. 2A, depicts a portion of motion-conducive equipment in the form of a tread deck 115, such as a pedal under an additional body part 105 of the subject 106, specifically the foot. In the illustrated embodiment shown in FIG. 2A, the at least one body part 104 is the leg of the subject, which includes a thigh 104a, a lower leg 104c, and a knee joint 104b connecting the thigh 104a and the lower leg 104c together. The flexible compression garment 102 defines an exterior 120, an interior surface 124, and the one or more actuators 110 are configured as a single coiled actuator extending about a portion of the exterior 120 of the flexible compression garment 102. For example, the single coiled actuator can extend circumferentially about and along the exterior 120 of the flexible compression garment 102 in a substantially helical path and is positioned and configured to increase or decrease an interior space 122 (FIG. 2B) defined by an interior surface 124 (FIG. 2B) of the flexible compression garment 102 responsive to actuation thereof. However, in other embodiments, the one or more actuators 110, such as the single coiled actuator, can be embedded internally within the flexible compression garment 102. In an embodiment, the flexible compression garment can include a plurality of actuators 110 that each extend circumferentially about the at least one flexible compression garment, and function similar or identical to any actuator described herein.

As illustrated in FIGS. 1A and 2A, the motion-conducive equipment 103 can be a cycle that includes one or more sensors 108, 108', or 108" positioned on or at least partially embedded within the motion-conducive equipment 103. Suitable cycles can include a bicycle (e.g., a road bicycle, a mountain bicycle, etc.), a unicycle, a tricycle, a recumbent cycle, or an exercise cycle (e.g., a stationary cycle, or a recumbent stationary cycle). As shown, one or more of the tread deck 115 (e.g., pedal), the handle 117 (e.g., handlebars), or seat 119 can carry at least one of the one or more sensors 108, 108', and 108" which can be any of the sensors described herein. For example, the motion-conducive equipment 103 in the form of a bicycle can include sensors 108, 108', or 108" in one or more of the tread decks 115 (e.g., pedals), one or more sensors 108' in the handles 117 (e.g., handlebars or grips thereof), or one or more sensors 108" can be positioned on the seat 119 of the bicycle. In an embodiment, the motion-conducive equipment 103 can include the control system 112 positioned on or at least partially embedded within the surface of the motion-conducive equipment 103. The control system 112 can be configured substantially identically or similarly to any control system 112 described herein. In an embodiment, the one or more sensors 108 can include a pedometer, wherein the control system 112 is configured to activate the actuators 110 of the flexible compression garment 102 upon occurrence of a specific number of rotations of the pedals. In an embodiment, the one or more sensors 108 can include a pressure sensor, wherein the control system 112 is configured to activate the actuators 110 of the flexible compression garment 102 upon occurrence of a sensed pressure on individual pedals or cumulative pressure applied on one or more of the pedals.

Figure 2B:
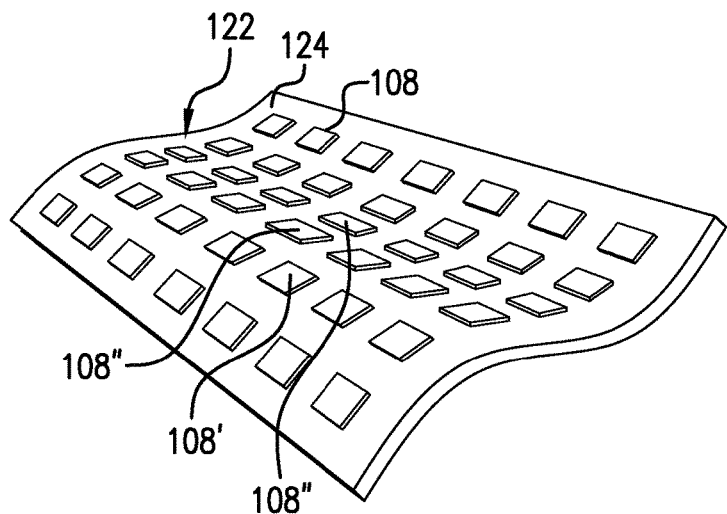
FIG. 2B is an isometric cutaway view of a section of the flexible compression garment shown in FIG. 2A.

Referring to FIG. 2B, optionally, in some embodiments, one or more sensors 108, 108', or 108" can also be positioned on or at least partially embedded within the interior surface 124 of the flexible compression garment 102. The one or more sensors 108 or 108" can be configured similar or identical any sensor described herein. For example, when at least some of the sensors 108 are configured as acoustic sensors for sensing acoustic emission from the knee joint 104c, such sensors 108 can be positioned on or in the interior surface 124 of the flexible compression garment 102 so that they are located at or near the knee joint 104b (or other joint, such as one that can be affected by arthritis) and labeled as sensors 108" in FIG. 2B as merely an example.

Figure 2C:
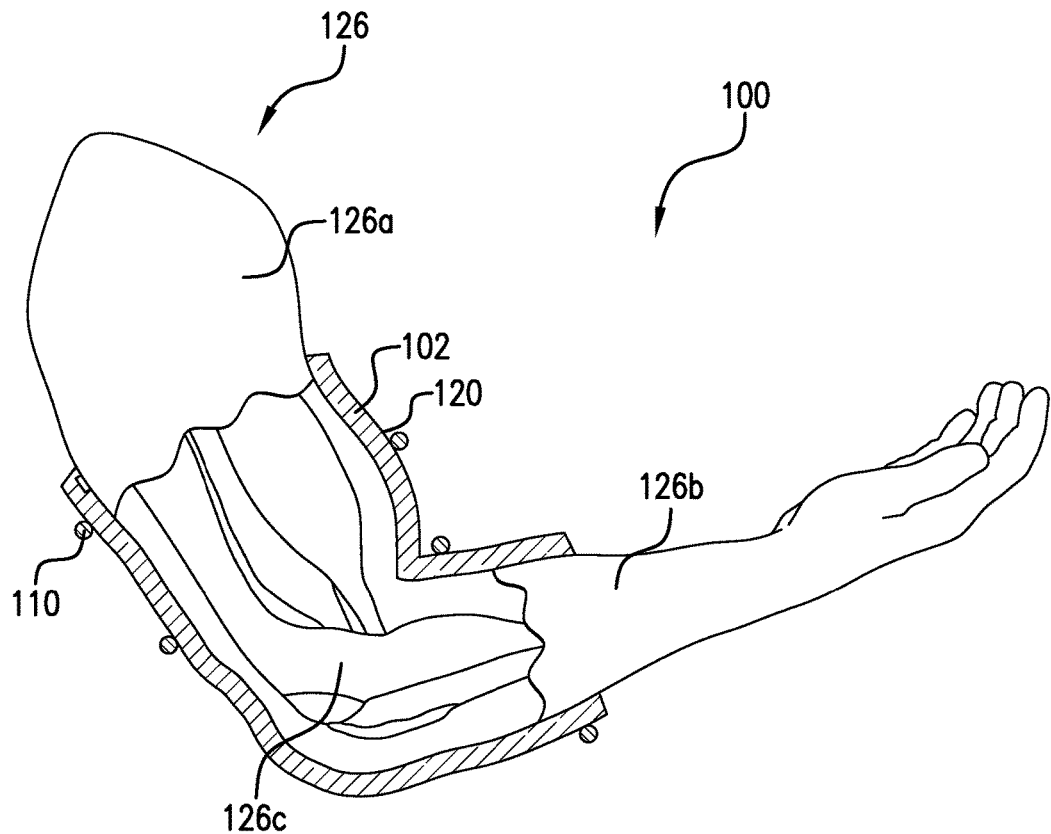
FIG. 2C is a side cutaway view of a flexible compression garment worn on an arm of a subject according to an embodiment.
Figure 2D:
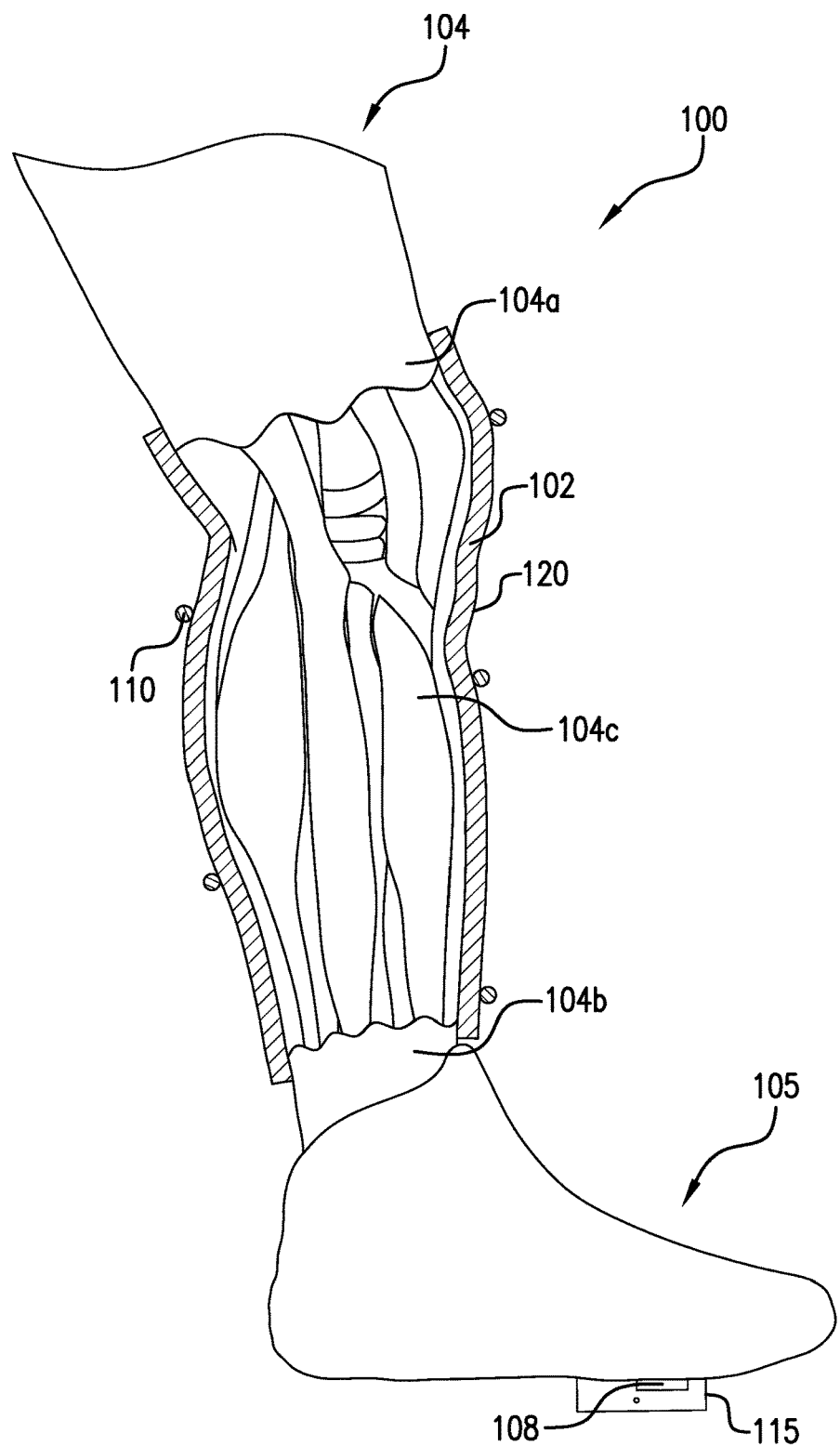
FIG. 2D is a side cutaway view of an embodiment of a garment system including a flexible compression garment worn on a leg of a subject and a portion of motion-conducive equipment in contact with the subject.

As previously described, the garment systems disclosed herein can be used on a number of different body parts besides a leg. For example, the at least one body part 104 can include a portion of an upper arm, a portion of an elbow, a portion of a forearm, a portion of a hand, a portion of a foot, a portion of a torso, or a portion of a neck. FIG. 2C is an isometric cutaway view of an embodiment of the flexible compression garment 102 worn on an arm 126 of the subject 106. The flexible compression garment 102 can be configured to extend around an upper arm 126a, a forearm 126b, and an elbow 126c that connects the upper arm 126a and forearm 126b together. In an embodiment, one or more wearable devices 113 can be worn on the same body part as the at least one flexible compression garment 102, a different or separate body part than the at least one flexible compression garment 102, or both. As another example, FIG. 2D is a side cutaway view of an embodiment of the flexible compression garment 102 configured to be worn on a lower leg 104b and at least a portion of an ankle of the subject 106 and the at least one sensor 108 supported by the tread deck 115 (e.g., pedal) under the additional body part 105 (e.g., foot) of the subject. Of course, in other embodiments, the flexible compression garment 102 can be configured for other body parts, such as the upper arm and shoulder, or neck of the subject 106. In other embodiments, the flexible compression garment 102 can be configured for other body parts that do not include a joint, such as a portion of a limb including, but not limited to all or part of, a thigh, a calf, a forearm, or an upper arm of the subject 106.

The motion-conducive equipment 103 can be configured as any equipment suitable for movement thereon or therewith, such as by way of non-limiting example, a cycle, a treadmill, an elliptical trainer, a rowing machine, a stair climber, a flexion-based exercise machine, one or more weights, a pulley, a punching bag, a resistance-training apparatus, a ball-driving implement, an object-striking implement, or a pull-up bar. Additionally, motion-conducive equipment can include a manually propelled conveyance, such as a wheelbarrow, a walker, a cane or other walking aid, a shopping cart, a stroller, a wagon, a wheel chair; or a manually propelled tool, such as a lawn mower (e.g., non-self-propelled lawn mower), a vacuum, a rake, or a shovel. In some embodiments, motion-conducive equipment—including exercise equipment, a manually propelled conveyance, or a manually propelled tool—can include an automated or motorized portion to assist or resist motion or movement thereon. For example, a treadmill can have a motor configured to make the tread surface rotate around the tread deck or raise or lower the level of inclination of the tread deck, a rowing machine or exercise cycle can have an automatically controlled resistance, or a lawn mower can be at least partially self-propelled.

In some embodiments, motion-conducive equipment having an automated or a motorized portion can include an equipment controller configured to control the motor or one or more movement properties including but not limited to, resistance, angle of inclination, speed of movement, duration of movement, path of motion of the movement. Movement properties can also include movements or exercises on or using motion-conducive equipment and every discrete movement therein (e.g., running or the discrete movement of lifting a leg during running), whether by the motion-conducive equipment or the subject. In an embodiment, the equipment controller is operably coupled to the control system of the garment system. The equipment controller can send one or more indication signals to the control system indicating that an alteration in one or more movement properties is imminent. In an embodiment, the equipment controller can include equipment programming instructions. Equipment programming instructions can include or be based upon one or more selected movement properties. For example, equipment programming instructions can include a selected duration of movement on a piece of motion-conducive equipment (e.g., workout duration), a selected level of exertion as sensed by the one or more sensors, a selected pace or speed on the motion-conducive equipment, a selected amount of force applied to one or more sensors on the motion-conducive equipment, a selected incline of at least a portion of the motion-conducive equipment, a selected resistance by a portion of the motion-conducive equipment, a selected path of motion or movement (e.g., form), or any other suitable movement property. Equipment programming instructions can be entered through the user interface, the equipment controller, or be stored in the memory of the control system.

In an embodiment, the control system (e.g., the control electrical circuitry) can also control the equipment controller operably coupled thereto responsive to one or more sensing signals. For example, the control system can direct the equipment controller to alter one or more movement properties and actuate one or more actuators responsive to one or more sensing signals. In an embodiment, the control system is configured to direct the equipment controller to automatically select, alter, or adjust one or more movement properties based on one or more of at least one sensed characteristic or at least one sensed movement property. For example, the equipment controller can be used to determine and effectuate alteration of resistance at the crank of an exercise bicycle based on one or more of the duration of the movement of a subject thereon, distance (or equivalent distance) travelled by the subject, the pressure exerted by the subject on the sensors on the pedals of the exercise bicycle, or the current resistance at the crank of the exercise bicycle. Further, one or more actuators of the flexible compression garment can be controlled in response to any of the above, such as responsive to the indication signal that a change in one or more movement properties is imminent. FIGS. 2E-2I depict some non-limiting embodiments of motion-conducive equipment that can include one or more sensors, control systems, or equipment controllers.

Figure 2E:
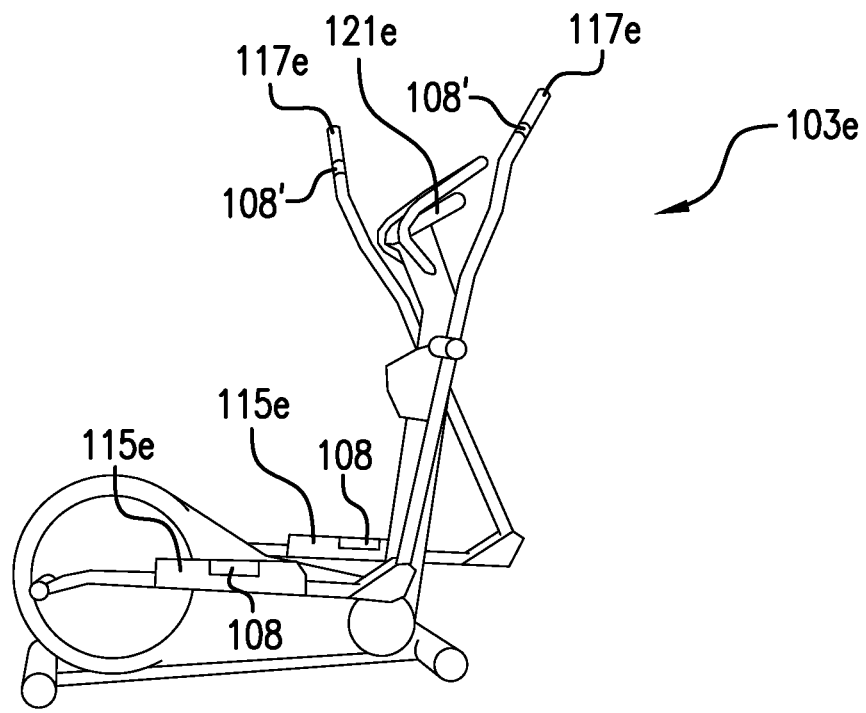
FIG. 2E is an isometric view of motion-conducive equipment of a garment system according to embodiment.

FIG. 2E is an isometric view of an embodiment of the motion-conducive equipment 103e configured as an elliptical trainer. The elliptical trainer can include, an equipment controller 121e, one or more handles 117e, and one or more tread decks 115e. The elliptical trainer can include one or more sensors 108, 108', or 108" therein or thereon. For example, as shown, the one or more sensors 108, can be at least partially embedded within or positioned on one or more of the tread decks 115e, or the one or more sensors 108' can be at least partially embedded within or positioned on one or more of the handles 117e, such as embedded in one or more grips on the handles 117e. The grips described herein can be removable or fixedly attached to the handles described herein and can be made of any material suitable for use as a grip, such as rubber, plastic, foam, grip tape, etc. The motion-conducive equipment 103e can also carry or support the control system 112, including one or more components thereof (e.g., power supply, control electrical circuitry, or memory). For example, the control system 112 can be at least partially embedded within or positioned on a surface of the motion-conducive equipment 103e, such as on a control panel housing the equipment controller 121e of the motion-conducive equipment 103e.

Figure 2F:
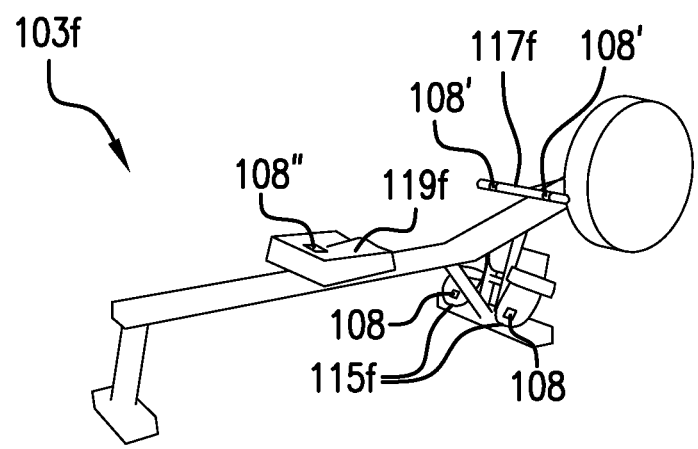
FIG. 2F is an isometric view of motion-conducive equipment of a garment system according to embodiment.

FIG. 2F is isometric view of an embodiment of the motion-conducive equipment 103f configured as rowing machine. The rowing machine can include, an equipment controller (not shown), a seat 119f, one or more handles 117f, one or more tread decks 115f, and one or more flywheels. The rowing machine can include one or more sensors 108, 108', or 108" therein or thereon. For example, as shown, the one or more sensors 108, can be at least partially embedded within or positioned on one or more of the tread decks 115f, the one or more sensors 108' can be at least partially embedded within or positioned on one or more of the handles 117f or a grip thereon, or the one or more sensors 108" can be at least partially embedded within or positioned on the seat 119f. The motion-conducive equipment 103f can also carry or support the control system 112, including one or more components thereof (e.g., power supply, control electrical circuitry, or memory). For example, the control system 112 can be at least partially embedded within or positioned on a surface of the motion-conducive equipment 103f, such as in or on the equipment controller (not shown).

Figure 2G:
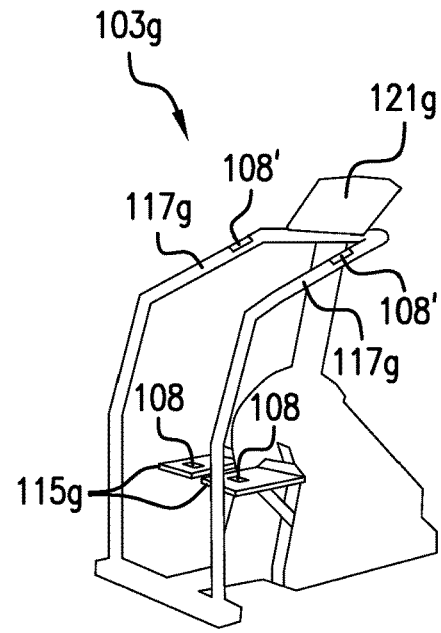
FIG. 2G is an isometric view of motion-conducive equipment of a garment system according to embodiment.

FIG. 2G is an isometric view of an embodiment of the motion-conducive equipment 103g configured as a stair climber or stair stepper machine. The stair climber can include, an equipment controller 121g, one or more handles 117g, and one or more tread decks 115g. The stair climber can include one or more sensors 108, 108', or 108" therein or thereon. For example, as shown, the one or more sensors 108, can be at least partially embedded within or positioned on one or more of the tread decks 115g, or the one or more sensors 108' can be at least partially embedded within or positioned on one or more of the handles 117g or grips thereon. The motion-conducive equipment 103g can also carry or support the control system 112, including one or more components thereof (e.g., power supply, control electrical circuitry, or memory). For example, the control system 112 can be at least partially embedded within or positioned on a surface of the motion-conducive equipment 103g, such as on the equipment controller 121g of the motion-conducive equipment 103g.

Figure 2H:
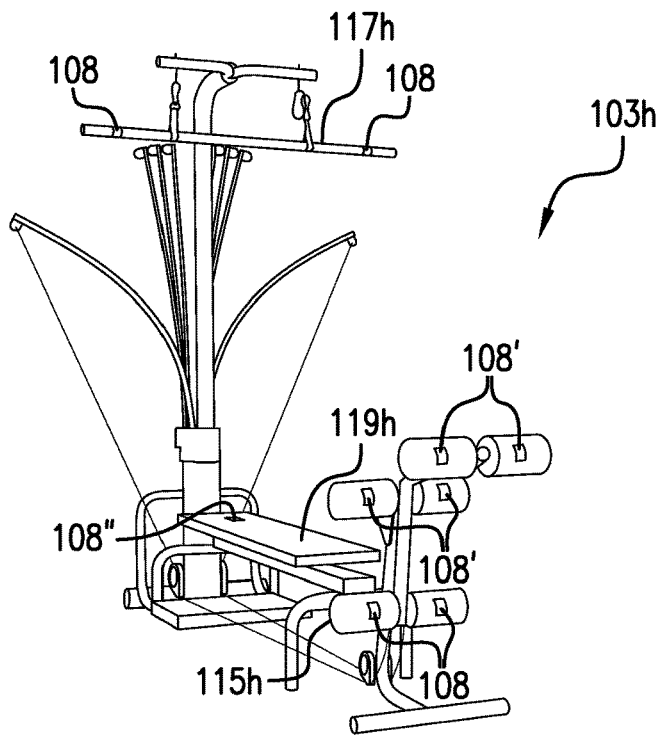
FIG. 2H is an isometric view of motion-conducive equipment of a garment system according to embodiment.

FIG. 2H is an isometric view of an embodiment of the motion-conducive equipment 103h configured as a flexion-based exercise machine. Suitable flexion-based exercise machines can include for example a BOWFLEX® exercise machine, a CROSSBOW™ by WEIDER®, or the like. The flexion-based exercise machine can include, one or more handles 117h, and one or more tread decks 115h. The flexion-based exercise machine can include one or more sensors 108, 108', or 108" therein or thereon. For example, as shown, the one or more sensors 108', can be at least partially embedded within or positioned on one or more of the tread decks 115h in the form of footrests or knee pads, the one or more sensors 108 can be at least partially embedded within or positioned on one or more of the handles 117h or grips thereon, or one or more sensors 108" can be at least partially embedded within or positioned on the seat 119h. The motion-conducive equipment 103h can also carry or support the control system 112, including one or more components thereof (e.g., power supply, control electrical circuitry, or memory). For example, the control system 112 can be at least partially embedded within or positioned on a surface of the motion-conducive equipment 103h.

Figure 2I:
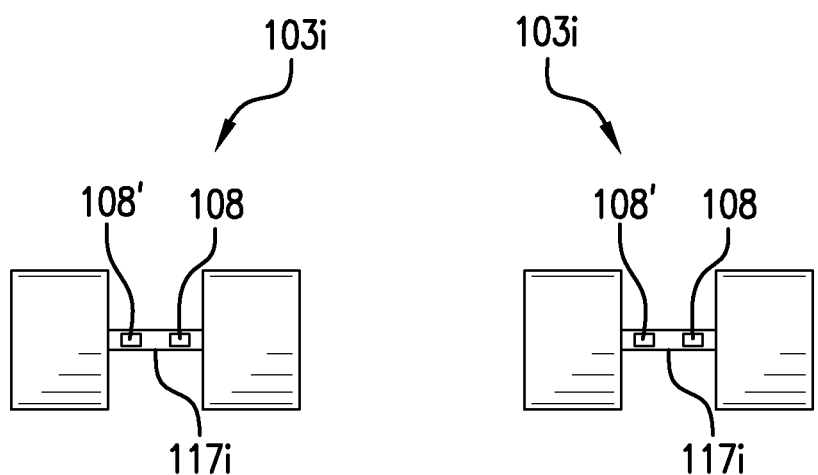
FIG. 2I is a front view of motion-conducive equipment of a garment system according to embodiment.

FIG. 2I is a front view of an embodiment of the motion-conducive equipment 103i configured as one or more weights (e.g., one or more dumbbells or barbells). The one or more weights can include one or more handles 117i. The one or more weights can include one or more sensors 108, 108', or 108" therein or thereon. For example, as shown, the one or more sensors 108, or 108' can be at least partially embedded within or positioned on one or more of the handles 117i or grips thereon. The motion-conducive equipment 103i can also carry or support the control system 112, including one or more components thereof (e.g., power supply, control electrical circuitry, or memory). For example, the control system 112 can be at least partially embedded within or positioned on a surface of the motion-conducive equipment 103i, such as in the one or more handles 117i.

Figure 2J:
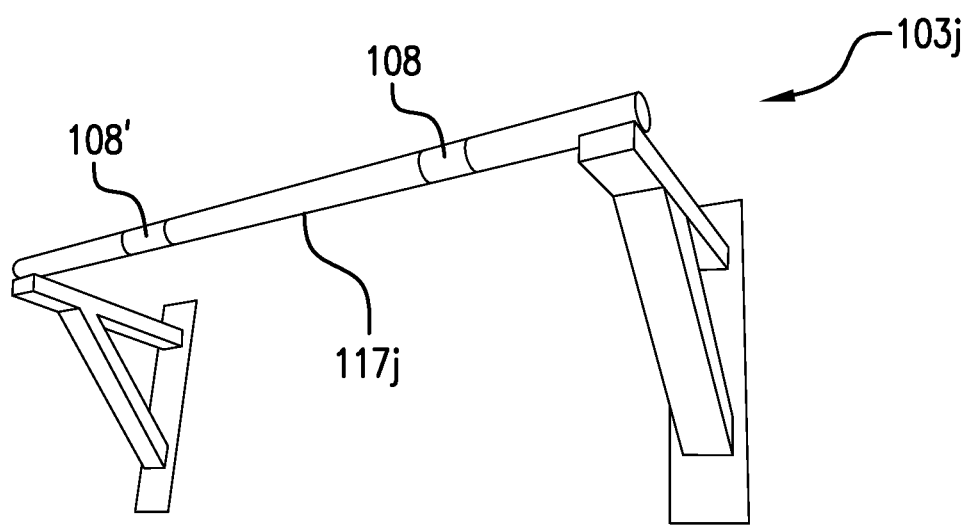
FIG. 2J is an isometric view of motion-conducive equipment of a garment system according to embodiment.

FIG. 2J is an isometric view of an embodiment of the motion-conducive equipment 103j configured as a pull-up bar. The pull-up bar can include one or more handles 117j. The pull-up bar can include one or more sensors 108, 108', or 108" therein or thereon. For example, as shown, the one or more sensors 108, or 108' can be at least partially embedded within or positioned on one or more of the handles 117j or grips thereon. The motion-conducive equipment 103j can also carry or support the control system 112, including one or more components thereof (e.g., power supply, control electrical circuitry, or memory). For example, the control system 112 can be at least partially embedded within or positioned on a surface of the motion-conducive equipment 103j, such as in the one or more handles 117j.

In an embodiment, a punching bag such as a dummy bag or speed bag can include one or more sensors 108 disposed therein or thereon. For example, a sensor 108 can be disposed in the apparatus holding the punching or speed bag in suspension or on the surface of or internal to the punching bag. An accelerometer can measure the increase in velocity from a punch, or a pressure sensor can measure the force delivered by a punch.

In an embodiment, a resistance-training apparatus, can include one or more sensors 108 disposed therein or thereon. A resistance training apparatus can include a football sled, resistance training chute or harness, or resistance bands. In an embodiment, one or more sensors 108 can be positioned on the pad of a football sled to measure the force applied to the sled or distance traveled by the sled. In an embodiment, a tension meter can be included on the harness of a resistance chute or resistance bands whereby the tension meter can detect the amount of tension applied thereto.

In an embodiment, a ball-driving implement, can include one or more sensors 108 disposed therein or thereon. The ball-driving implement can include a bat a golf club, a cricket bat, or a mallet. In an embodiment, one or more sensors 108 can be positioned on the striking face, head, or handle of the ball-driving implement. For example, a pressure sensor can be positioned on or in the head of a golf club, and the pressure sensor measures the amount of force applied to the face upon collision with a golf ball. As another example, a velocity sensor or accelerometer can be positioned on or in the head of a golf club, whereby the velocity sensor or accelerometer detect the amount of velocity or acceleration of the golf club head during a swing.

In an embodiment, an object-striking implement, can include one or more sensors 108 disposed therein or thereon. An object-striking implement can include a stick for striking, a mallet, a hammer, or a cudgel. For example, a pressure sensor can be positioned on or in the head of a hammer, whereby the pressure sensor measures the amount of force applied to the face upon collision with an object, the pressure sensor data can be used to determine if the force applied is decreasing over time and actuation of the flexible compression garment can be triggered responsive thereto. As another example, a velocity sensor or accelerometer can be positioned on or in the head of the hammer, whereby the velocity sensor or accelerometer detect the amount of velocity or acceleration of the hammer head during a swing.

It should be appreciated that further placements of the sensors 108, 108', or 108" on motion-conducive equipment (including any of the embodiments disclosed above) are contemplated herein, may not be limited to the explicitly described embodiments, and can be disposed in a location suitable to fulfill the function desired which can include specific positions or placements not explicitly recited.

Figure 3A:
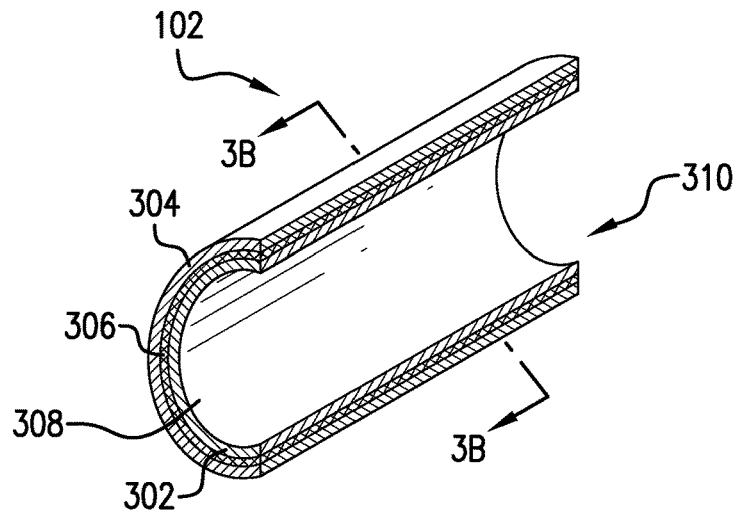
FIG. 3A is an isometric cutaway view of the flexible compression garment shown in FIG. 1A according to an embodiment.
Figure 3B:
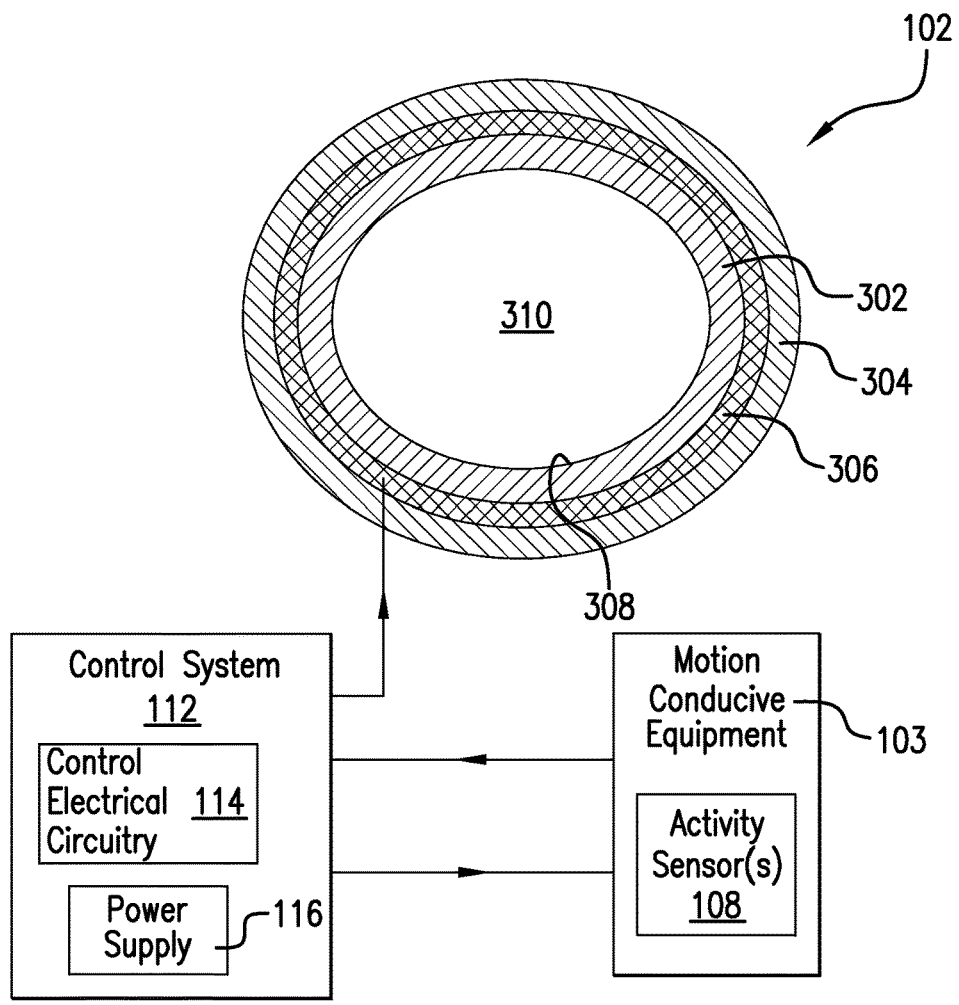
FIG. 3B is a cross-sectional view of the flexible compression garment shown in FIG. 3A taken along line 3B-3B thereof.

FIGS. 3A and 3B are isometric cutaway and cross-sectional views of the flexible compression garment 102 shown in FIGS. 1A and 1B according to an embodiment. In the illustrated embodiment, the flexible compression garment 102 includes an inner garment body 302, an outer garment body 304, and a substantially tubular actuator 306 disposed between the inner garment body 302 and the outer garment body 304 in a concentric arrangement. For example, the substantially tubular actuator 306 is illustrated as being embedded within the flexible compression garment 102 and held between the inner garment body 302 and the outer garment body 304. As merely an example, the substantially tubular actuator 306 can be made from a tube of electroactive polymer or a tube of shape memory alloy that is responsive to an appropriate actuation stimulus from the power supply 118 of the control system 112 so that a volume of an inner space 310 defined by the inner garment body 302 can increase or decrease responsive to actuation of the substantially tubular actuator 306.

In an embodiment, the one or more sensors can be disposed on or at least partially embedded in a piece of motion-conducive equipment 103. In an embodiment, the one or more sensors can be disposed on an interior surface 308 of the inner garment body 302 that defines the interior space 310. In embodiments, one or more sensors can be at least partially embedded within the inner garment body 302.

During use in some operational situations and responsive to the one or more sensors 108 of an associated piece of motion-conducive equipment 103 sensing the at least one characteristic (e.g., at least one characteristic associated with movement of the subject or at least one physiological characteristic of the subject), the control electrical circuitry 114 of the control system 112 directs the substantially tubular actuator 306 to selectively constrict, such as against the at least one body part 104 to provide more support thereto or to improve muscle or joint functioning. During use in other operational situations and responsive to the one or more sensors 108 of an associated piece of motion-conducive equipment sensing the at least one characteristic, the control electrical circuitry 114 of the control system 112 directs the substantially tubular actuator 306 to selectively dilate about the at least one body part 104, such as during a portion of an athletic activity in which the at least one body part of the subject is minimally exerted or stressed. During use in other operational situations, responsive to the one or more sensors 108 sensing the at least one characteristic, the control electrical circuitry 114 of the control system 112 directs the substantially tubular actuator 306 to selectively constrict or to selectively dilate, such as to aid a particular activity or action of the at least one body part 104. For example, the particular activity or action can be an athletic motion or action undertaken by at least one particular limb, such as a leg pushing against a tread deck or pedal.

Figure 3C:
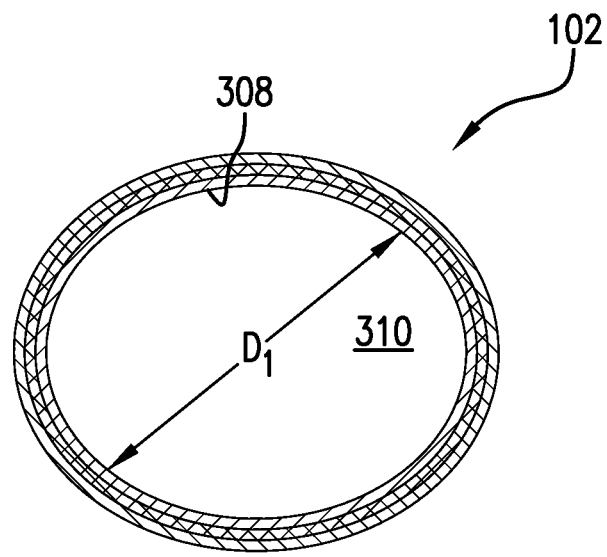
FIG. 3C is a cross-sectional view of the flexible compression garment shown in FIG. 3A prior to actuation of one or more actuators or at a low actuation level.
Figure 3D:
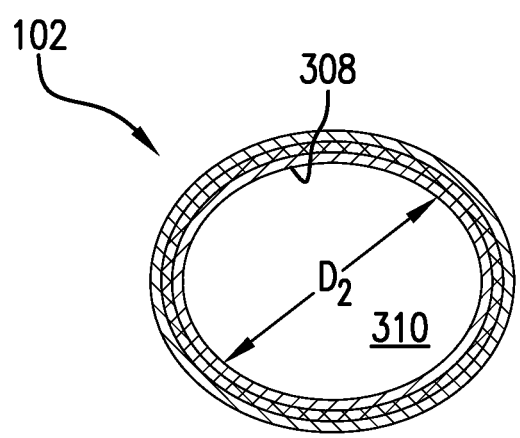
FIG. 3D is a cross-sectional view of the flexible compression garment shown in FIG. 3A after actuation of one or more actuators or at a relatively higher actuation level than in FIG. 3C.

FIGS. 3C and 3D are cross-sectional views of the flexible compression garment 102 shown in FIG. 3A prior to actuation (e.g., activation or direction) of the actuator 306 or at a low actuation level, and after actuation of the actuator 306 or at a relatively higher actuation level than in FIG. 3C, respectively. As shown in FIG. 3C, prior to actuation of the actuator 306 or at a low actuation level, the interior space 310 of the flexible compression garment 102 exhibits a relatively larger diameter D1 or other lateral dimension. As shown in FIG. 3D, after actuation of the actuator 306 or at a relatively higher actuation level than in FIG. 3C, the actuator 306 selectively constricts such that the interior space 310 of the flexible compression garment 102 exhibits a relatively smaller diameter D2 or other lateral dimension. This constriction of the flexible compression garment 102 can be used to apply selective amounts of compression forces to the at least one body part of the subject. For example, the actuator 306 can cause narrowing of substantially the entire flexible compression garment 102 to the smaller diameter D2. Conversely, actuation of the actuator 306 can cause the actuator 306 to selectively dilate, thereby dilating the interior space 310 from a smaller diameter D2 to a larger diameter D1 relieving compression forces on the at least one body part of the subject.

Figure 4:
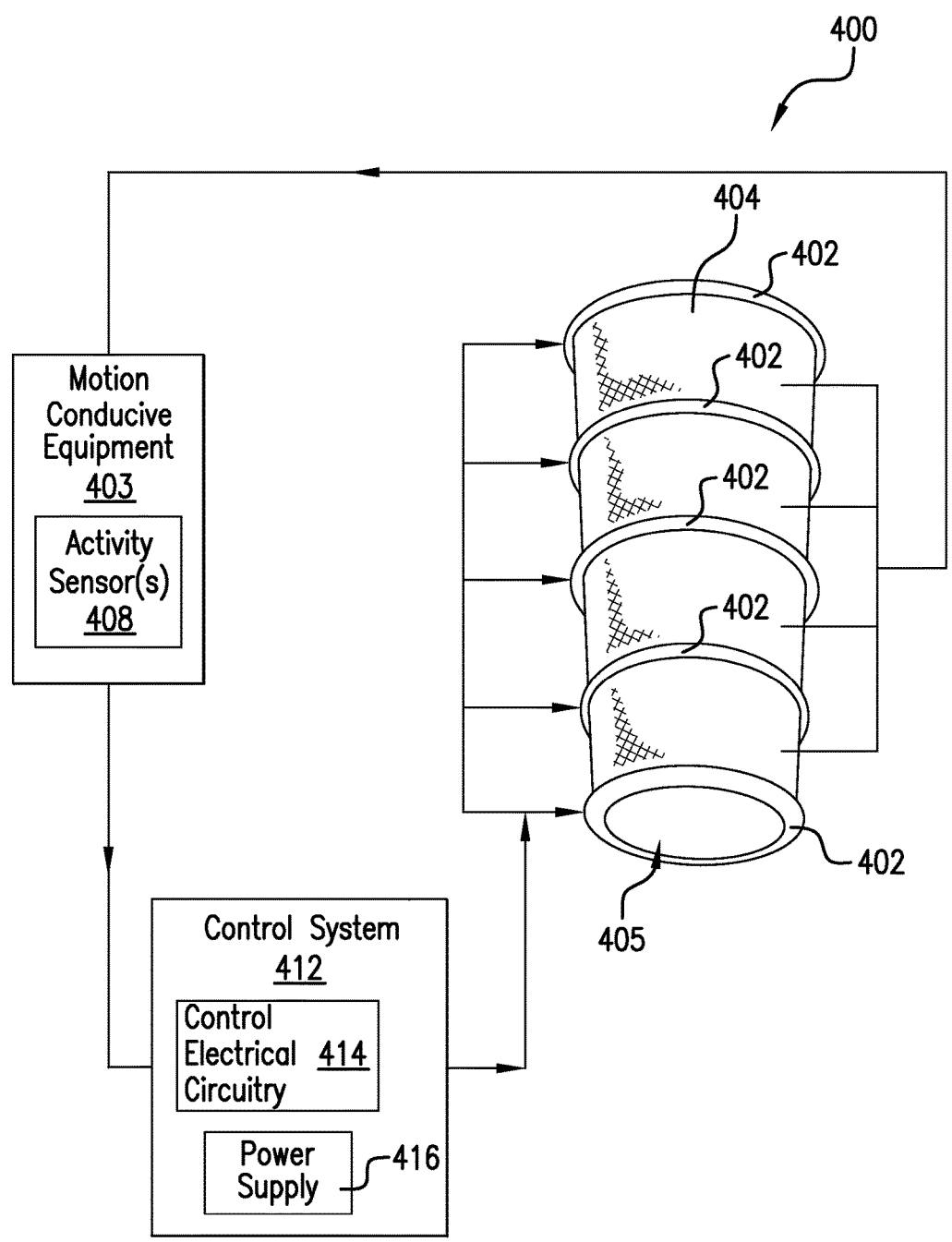
FIG. 4 is an isometric view of an embodiment of a garment system including a plurality of ring-shaped actuators.

FIG. 4 is an isometric view of an embodiment of a garment system 400 including a plurality of ring-shaped actuators 402. The garment system 400 includes a flexible compression garment 404 that can be made from the same materials as the flexible compression garment 102. The flexible compression garment 404 defines an interior space 405 for receiving at least one body part of a subject, such as an arm, leg, or other body part. The plurality of ring-shaped actuators 402 are longitudinally spaced from each other. In the illustrated embodiment, the plurality of ring-shaped actuators 402 are disposed circumferentially about an exterior of the flexible compression garment 404. However, in other embodiments, the plurality of ring-shaped actuators 402 can be at least partially embedded within the flexible compression garment 404. As merely an example, each of the plurality of ring-shaped actuators 402 can be made from a ring of electroactive polymer or a ring of shape memory alloy that is responsive to an appropriate actuation stimulus from a power supply 416 of a control system 412.

The garment system 400 further includes one or more sensors 408, which can be configured similar or identical to any of the sensors disclosed herein. In the illustrated embodiment, the one or more sensors 408 are disposed within or on a piece of motion-conducive equipment 403. The motion-conducive equipment 403 can be similar or identical to any motion-conducive equipment disclosed herein. In some embodiments, one or more sensors 408 can also be carried on or within a wearable device substantially as described herein.

The control system 412 is configured and functions similarly or identically to the control system 112 in FIG. 1. For example, the control system 412 is operably coupled to the one or more sensors 408 on the motion-conducive equipment 403 and the plurality of ring-shaped actuators 402 on the flexible compression garment 404. Thus, during use in some operational situations, responsive to the one or more sensors 408 sensing the at least one characteristic associated with movement of the subject or at least one physiological characteristic of the subject, the control electrical circuitry 414 of the control system 412 directs the plurality of ring-shaped actuators 402 to selectively constrict (e.g., compress against the at least one body part to provide more support thereto or to improve muscle or joint functioning). Thus, the actuation of each of the plurality of ring-shaped actuators 402 decreases a diameter thereof. During use in other operational situations, responsive to the one or more sensors 408 sensing the at least one characteristic associated with movement of the subject or at least one physiological characteristic of the subject, the control electrical circuitry 414 of the control system 412 directs the plurality of ring-shaped actuators 402 to selectively dilate (e.g., relieve compression against the at least one body part), such as during a portion of an athletic activity in which the at least one body part of the subject is exerted or stressed. Thus, the actuation of each of the plurality of ring-shaped actuators 402 increases a diameter thereof.

Figure 5:
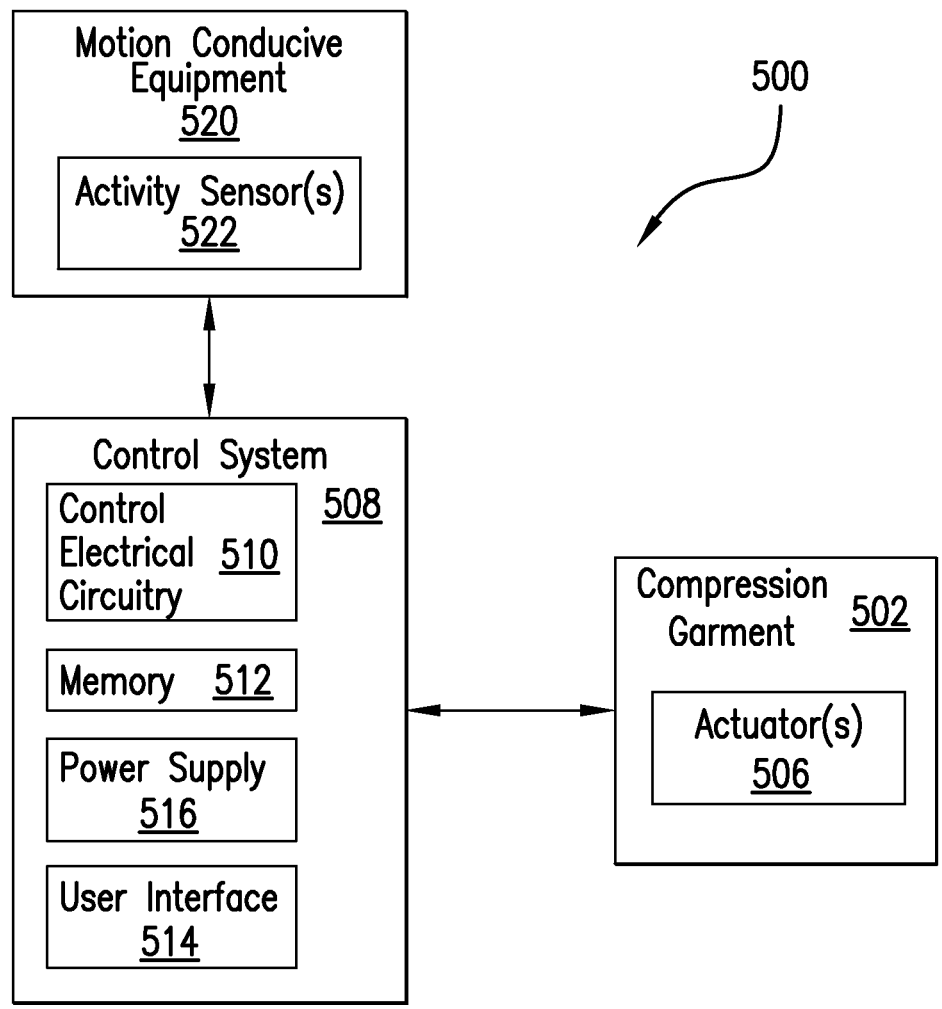
FIG. 5 is a functional block diagram of an embodiment of a garment system.

In some embodiments, the garment systems disclosed herein can include memory and a user interface that enables the subject or another person to program the manner in which an individual garment system operates. For example, FIG. 5 is a functional block diagram of an embodiment of a garment system 500. The garment system 500 includes a compression garment 502 including one or more actuators 506, as described in any of the embodiments disclosed herein. The garment system 500 includes a piece of motion-conducive equipment 520 including one or more sensors 522 configured to sense at least one characteristic associated with movement of the subject or at least one physiological characteristic of the subject as described in any of the embodiments herein. The garment system 500 further includes a control system 508 operably coupled to the one or more sensors 522 and the one or more actuators 506. The control system 508 includes control electrical circuitry 510 that controls the operation of the one or more sensors 522 or the one or more actuators 506; memory 512 operably coupled to the control electrical circuitry 510 that can be programmed with instructions via a user interface 514; and a power supply 516 that powers some or all of the components of the garment system 500.

The memory 512 can be configured to store one or more of sensing data, sensing data corresponding to the one or more sensing signals, actuation data corresponding to the selective constriction or selective dilation of the at least one flexible compression garment, operational programs, threshold levels, one or more selected profiles, one or more selected activities, motion-conducive equipment (e.g., type of motion-conducive equipment) in use or patterns associated therewith, or other data related to the operation of the garment system 500. The memory 512 can be programmed via the user interface 514 with operational programs for the operation of the garment system 500, threshold levels, actuation data corresponding to selective contraction or selective dilation, sensing data, one or more selected activities, one or more selected profiles, one or more pieces of motion-conducive equipment, or other data. For example, the user interface 514 can include a keypad, monitor, touch screen, voice command recognition, desktop computer, laptop computer, cell phone, or combinations thereof operably coupled to the control electrical circuitry 510 of the control system 508. The user interface 514 can be operably coupled to the control electrical circuitry 510 via a wireless or wired communication connection. The subject that wears the garment system 500 or another party (e.g., a trainer or a medical professional) can program instructions into the memory 512 for the operation of the one or more sensors 522, motion-conducive equipment 520, and the one or more actuators 506 via the user interface 514 either locally or remotely from the subject or the motion-conducive equipment. The user interface can be local or remote from the subject or the motion-conducive equipment. Any methods of operation for any of the garment systems disclosed herein can be programmed into the memory 512, as needed or desired. In an embodiment, the memory 512 is configured to store sensing data corresponding to the one or more sensing signals output from the one or more sensors 522, one or more selected profiles, or actuation data corresponding to the executed selective constriction or the selective dilation of the flexible compression garment 502. Such sensing data, selected profiles, and actuation data can be downloaded or uploaded by the subject or other person (e.g., a medical professional) for analysis or use, such as through the user interface 514. A selected profile can include selected one or more of subject age, subject preferences, a target pace, a target pulse, a target distance of travel, a duration of movement, or an intensity of movement.

During operation, the control circuitry 510 accesses and receives instructions (e.g., operational programs) from the memory 512 and directs the sensing operations of the one or more sensors 522 or actuation of the one or more actuators 506 at least partially based on the instructions. For example, responsive to the instructions stored in the memory 512, the control system 508 can direct the one or more actuators 522 to cause the compression garment 502 to selectively constrict at least one portion of the compression garment 502 responsive to the one or more sensors 522 sensing at least one characteristic associated with movement of the subject or at least one physiological characteristic of the subject. As another example, responsive to the instructions stored in the memory 512, the control system 508 can direct the one or more actuators 522 to cause the compression garment 502 to selectively dilate at least one portion of the flexible compression garment 502 responsive to the one or more sensors 522 sensing the at least one characteristic associated with movement of the subject or at least one physiological characteristic of the subject.

In an embodiment, the memory 512 stores sensing data corresponding to the one or more sensing signals from the one or more sensors 522 and stores actuation data corresponding to the selective constriction or the selective dilation of the flexible compression garment 502, which can be downloaded or uploaded at any of the user interfaces 514 disclosed herein (e.g., a cell phone, desktop computer, laptop computer, or other computing device). For example, at the user interface 514, a person can download the sensing data and the actuation data such as frequency and duration of constriction or dilation of the flexible compression garment 502, or the sensing signals received from the one or more sensors 522.

The garment systems disclosed herein can also be used in conjunction with a motion sensing system for monitoring, teaching, or correcting a subject's movement during different activities, such as walking, running, jumping, cycling, or any other specific activity or motion. For example, the one or more sensors 522 associated with the motion-conducive equipment 520 can be configured to sense at least one characteristic associated with movement of the subject or at least one physiological characteristic of the subject, or track physical movement of the subject, such as motion of one or more limbs of the subject. For example, such physical movement can be movement of a pulling, pushing, or running motion. In an embodiment, the one or more actuators 506 are configured to selectively constrict or dilate upon receiving one or more actuation signals, responsive to sensing the at least one characteristic related to physical movement of the subject. In an embodiment, the user interface 514 is configured to allow a person to input sensing data into the memory 512 of the control system 508 and associate (e.g., directly designate or label the data set or as yet sensed data) the sensing data with one or more of the selected profiles or attributes stored in the memory 512. In an embodiment, the control electrical circuitry 510 is configured to automatically associate or correlate the sensing data with one or more of the selected profiles stored in the memory 512 based on recognized or template patterns of the sensing data stored in the memory 512 known to correspond to a particular one or more specific selected profiles, by comparison therebetween. For example, the control electrical circuitry 510 can associate a sensed pattern of running with the specific desired running form or motion based on comparison of stored baseline sensing data previously known to correlate with the desired running form or motion. In an embodiment, the control system can automatically select at least one operational program responsive to the correlated at least one selected profile.

In operation, responsive to receiving one or more sensing signals from the one or more sensors 522, the control electrical circuitry 510 of the control system 508 directs the one or more actuators 506 to actuate, thereby causing the flexible compression garment 502 to selectively constrict or selectively dilate. The selective constriction or dilation is provided to direct, support, or aid the subject's movement to substantially correspond to a stored movement, activity, selected profile, or movement pattern in the memory 512 of the control system 508. For example, the stored movement or movement pattern can be a model or desired form (e.g., optimum stride form for long distance running) or other athletic movement as input via the user interface 514 by the subject or another person. The selective constriction or dilation (e.g., around the subject's leg) is provided to direct, support, or aid the subject's movement during the activity stored in the memory 512. Thus, the garment system 500 can serve to assist training the subject in specific movements for sporting activities, or general movement such as walking for physical therapy. In another embodiment, responsive to receiving the output from the one or more sensors 522 via one or more sensing signals, the memory 512 can be programmed with or select at least one operational program according to which the actuating the one or more actuators 506 occurs.

Figure 6:
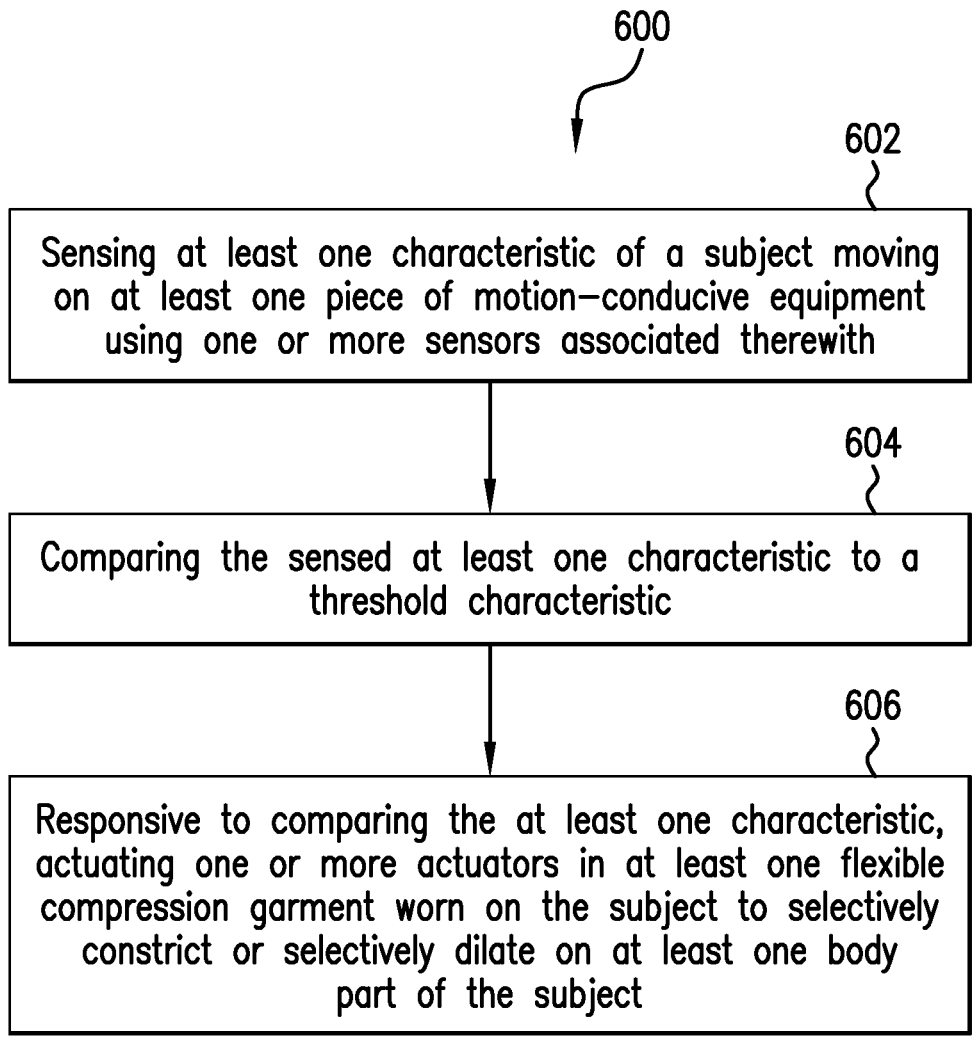
FIG. 6 is a flow diagram of an embodiment of a method of selectively constricting or dilating a flexible compression garment responsive to sensing feedback from one or more sensors.

FIG. 6 is a flow diagram of an embodiment of a method 600 of selectively controlling a compression garment. The method includes selectively constricting or selectively dilating a flexible compression garment (e.g., compressing or relieving compression of at least one body part of a subject) responsive to sensing feedback from one or more sensors disposed on a piece of motion-conducive equipment. Instructions for any of the methods disclosed herein can be stored in memory of a garment system such as the memory 512 of the garment system 500.

The method 600 includes an act 602 of sensing the at least one characteristic of a subject moving on at least one piece of motion-conducive equipment using one or more sensors associated therewith. In an embodiment, the act 602 of sensing the at least one characteristic includes sensing the at least one characteristic at a discrete point in time, over a period of time, or combinations thereof. In an embodiment, the method further includes relaying or sending sensing signals from the sensors to the control system, such as to the control electrical circuitry.

As previously discussed, the at least one characteristic can include at least one of the a physical characteristic, a chemical characteristic (e.g., biochemical or biological), a physiological characteristic of the subject, a change in motion of travel of the subject (e.g., a change in direction of travel of the subject, a change in velocity of the subject, a change acceleration of the subject), a load applied to the one or more sensors by a body part of the subject, pressure applied to the one or more sensors by a body part of the subject, tension applied to the one or more sensors by a body part of the subject, torque applied to the one or more sensors by a body part of the subject, a load on a body part of the subject, pressure on a body part of the subject, tension on a body part of the subject, pulse in a body part of the subject, velocity of at least a body part of the subject, acceleration of at least a body part of the subject, velocity of at least a portion of the motion-conducive equipment, acceleration of at least a portion of the motion-conducive equipment, location of the subject, gait of the subject, motion (e.g., repetitive motion) of at least one body part of the subject, pace at which the subject moves, distance that the subject has traveled, nerve activity of the subject, chemical excretion (e.g., amount or type) of the subject, temperature in a body part of the subject, heart rate of the subject, pulse in a body part of the subject, temperature of the ambient environment of the subject, oxygenation of a body part of the subject, acoustic emission from at least one joint or muscle of the subject, location of the subject, variations or patterns of any of the foregoing, or any other characteristic described herein. Furthermore, in one or more embodiments, the one more sensors can sense only the muscle activity (e.g., one or more muscle sensors) or sense only joint activity (e.g., one or more joint sensors).

The method 600 also includes an act 604 of, comparing the sensed at least one characteristic to a threshold characteristic. Comparing the sensed at least one characteristic to a threshold characteristic, can be carried out by the control system as described herein. For example, the control electrical circuitry can receive a signal from one or more sensors indicating the sensed at least one characteristic and compare the at least one characteristic to a threshold characteristic (e.g., a threshold value of the at least one characteristic) in look-up tables or operational programs stored in the memory. In an embodiment, comparing the sensed at least one characteristic to a threshold characteristic can include determining if the sensed at least one characteristic is above or below a minimum or maximum threshold value thereof, such as a minimum or maximum value for increasing or decreasing the difficulty or resistance of applied by the motion-conducive equipment (e.g., maximum or minimum amount of time in motion, force exerted, respiration rate, heart rate, hydration level, etc.), or a minimum or maximum value for safety. In an embodiment, the control electrical circuitry can automatically compare the sensed at least one characteristic with previously sensed levels of the at least one characteristic to determine similarities or variations therein. Such similarities or variations can be used to determine if the movement should continue or be terminated or if the actuators should be actuated.

In an embodiment, the method can further include associating or correlating, with the control electrical circuitry, sensing data including one or more of the at least one characteristics with at least one selected motion-conducive equipment in the memory. In an embodiment, the method 600 included automatically selecting, with the control system, the at least one operational program or equipment operational program. Automatically selecting, with the control system, the at least one operational program can be based on or responsive to the at least one selected motion-conducive equipment associated or correlated with the sensing data. Automatically selecting the operational program can be based on a comparison, by the control electrical circuitry, of the sensing data with baseline levels or patterns of the sensed at least one characteristic known to correlate with the motion-conducive equipment to determine a substantial match therebetween.

The method 600 also includes an act 606 of, responsive to comparing the at least one characteristic with a threshold characteristic, actuating one or more actuators in at least one flexible compression garment worn on the subject to selectively constrict or selectively dilate on at least one body part of the subject. Actuating the one or more actuators in at least one flexible compression garment worn on the subject to selectively constrict or selectively dilate on at least one body part of the subject, includes actuating the one or more actuators to selectively constrict or selectively dilate around at least one body part of the subject on which the at least one flexible compression garment is worn. Actuating the one or more actuators can be carried out via sending an actuation signal from the control system to the one or more actuators or the power supply, such as from the control electrical circuitry. In an embodiment, actuating the one or more actuators can be carried out during movement of the subject (e.g., during continued participation in an activity that the subject is participating in while the sensors detect the data) or during inactivity of the subject, such as only during movement or only during inactivity of the subject. For example, in an embodiment, actuating the one or more actuators (e.g., activating, causing, or directing) to selectively constrict or dilate is responsive to the at least one characteristic sensed by one or more sensors being over or below a threshold level. The at least one characteristic and associated threshold level can be any described herein, such as indicative of the at least one subject or muscle being injured, exerted, or strained past a selected limit. For example, such a threshold level can be stored in the memory of a garment system such as the memory 512 of the garment system 500 shown in FIG. 5.

In an embodiment, actuating the one or more actuators can be responsive to sensing the at least one characteristic via the one or more sensors. For example, the threshold characteristic can be any level for a particular characteristic, such as any level above zero such that the actuators are at least partially actuated by mere detection of at least one characteristic indicative of the subject using the piece of motion-conducive equipment.

In an embodiment, actuating the one or more actuators includes applying voltage or current from the power supply to the one or more actuators to cause actuation thereof. In an embodiment, actuating the one or more actuators can be carried out substantially in cycle, concert, or rhythm with the at least one characteristic sensed by the one or more sensors (e.g., actuating in rhythm with a pulse in a body part, heartbeat, or gait of the subject) or changes therein (e.g., increases or decreases in the sensed at least one characteristic).

In an embodiment, actuating the one or more actuators occurs according to an operational program, and can be initiated responsive to a sensed at least one characteristic. In some embodiments, the operational program is a pre-programmed operational program. In an embodiment, the at least one operational program can be related to (e.g., based upon, associated with, selected upon detection of, or correlated with) one or more of, the motion-conducive equipment, a selected profile, at least one movement property, a selected activity, a sensed characteristic (e.g., a detected gait, a detected pulse), an elapsed time, a detected force exerted, a detected velocity, a detected acceleration, or a detected distance travelled, (e.g., equivalent to distance traveled if using stationary equipment as motion-conducive equipment). In an embodiment, actuating the one or more actuators includes automatically selecting, via the control system (e.g., computer control system), the at least one operational program responsive to one or more of a selected profile, at least one sensed characteristic (e.g., a gait; a pace; a time; a position; a passage of an amount of time; a distance traveled; an amount of force exerted on a sensor such as an amount of load on a body part or an amount of tension on a body part; or a movement), or a selected activity associated with the sensing data. In an embodiment, the at least one operational program can be selected from multiple operational programs having one or more different actuation criteria, pulse constriction or dilation rates, constriction or dilation strengths, or constriction or dilation durations. In an embodiment, the method 600 can also include an act of programming (e.g., uploading, selecting, writing, or designating) the at least one operational program into the control system, such as via the user interface.

In an embodiment, the method 600 can include an act of wearing at least one flexible compression garment of a garment system on at least one body part of a subject. The at least one flexible garment includes one or more actuators configured selectively constrict or selectively dilate. For example, the at least one body part on which the at least flexible compression garment is worn includes at least a portion of an arm, at least a portion of a forearm, at least a portion of a wrist, at least a portion of a thigh, at least a portion of a lower leg, a least a portion of a knee, at least a portion of an ankle, at least a portion of a foot, at least a portion of a neck, or at least a portion of a chest.

In an embodiment, the method 600 can include the act of moving, using at least one piece of motion-conducive equipment. The motion-conducive equipment includes one or more activity sensors configured to sense at least one characteristic associated with movement of the subject or at least one physiological characteristic of the subject during one or more of movement or inactivity. The motion-conducive equipment can include any of the sensors described herein, such as those used in the garment system 100 shown in FIG. 1A. In an embodiment, the motion-conducive equipment can include any of the motion-conducive equipment disclosed herein. In an embodiment, movement on the motion-conducive equipment can include using a piece of motion-conducive equipment for the motion-conducive equipment's intended purpose, such as running on a treadmill, pushing a wheel chair, or pedaling a cycle.

The method 600 can include an act of providing at least one flexible compression garment of a garment system, with the at least one flexible compression garment being wearable on at least one body part of a subject as described herein. The method 600 can include an act of providing motion-conducive equipment of a garment system (e.g., associated with the garment system). The motion-conducive equipment can be identical or similar to any motion-conducive equipment described herein. In an embodiment, providing the motion-conducive equipment includes positioning or replacing at least one of the one or more sensors with one or more additional (e.g., new or different) sensors than used previously.

In an embodiment, the method 600 can include positioning (e.g., placing or putting) the at least one flexible compression garment on at least one body part of the subject. In an embodiment, the method 600 can include positioning (e.g., placing or putting) the subject on the motion-conducive equipment.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A garment system, comprising:
   at least one flexible compression garment configured to be worn on at least one body part of a subject, the at least one flexible compression garment defining an interior space configured to receive the at least one body part;
   motion-conducive equipment;
   one or more sensors disposed on or in the motion-conducive equipment, the one or more sensors configured to sense at least one characteristic associated with movement of the subject or at least one physiological characteristic of the subject, the one or more sensors further configured to output one or more sensing signals indicative of the at least one characteristic;
   one or more actuators positioned relative to the at least one flexible compression garment and configured to selectively constrict or selectively dilate the at least one flexible compression garment; and
   a control system operably coupled to the one or more actuators and further operably coupled to the one or more sensors to receive the one or more sensing signals therefrom, the control system including control electrical circuitry configured to direct the one or more actuators to selectively constrict or selectively dilate the at least one flexible compression garment responsive to the one or more sensing signals from the one or more sensors.

2. The garment system of claim 1, wherein at least one of the one or more sensors are integrally formed on the motion-conducive equipment.

3. The garment system of claim 1, wherein at least one of the one or more sensors are removably secured to the motion-conducive equipment.

4. The garment system of claim 1, wherein the motion-conducive equipment includes a cycle, a treadmill, an elliptical trainer, a rowing machine, a stair climber, a flexion-based exercise machine, one or more weights, a pulley, a punching bag, a pull-up bar, a resistance training apparatus, a ball-driving implement, an object-striking implement, or a manually propelled conveyance.

5. The garment system of claim 1, wherein the motion-conducive equipment includes a treadmill and at least one of the one or more sensors are disposed on or in a tread deck of the treadmill.

6. The garment system of claim 1, wherein the motion-conducive equipment includes a cycle and at least one of the one or more sensors are disposed on or in at least one of one or more pedals, a seat, or handlebars of the cycle.

7. The garment system of claim 1, wherein the motion-conducive equipment includes an elliptical trainer and at least one of the one or more sensors are disposed on or in one or more tread decks or handles of the elliptical trainer.

8. The garment system of claim 1, wherein the motion-conducive equipment includes a rowing machine and at least one of the one or more sensors are disposed on or in at least one of at least one tread deck or a handle of the rowing machine.

9. The garment system of claim 1, wherein the one or more sensors are configured to detect one or more of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, a load on a body part of the subject, pressure on a body part of the subject, tension on a body part of the subject, pulse in a body part of the subject, velocity of at least a body part of the subject, acceleration of at least a body part of the subject, velocity of at least a portion of the motion-conducive equipment, acceleration of at least a portion of the motion-conducive equipment, location of the subject, gait of the subject, pace at which the subject moves, distance that the subject has traveled, nerve activity of the subject, chemical excretion of the subject, temperature in a body part of the subject, heart rate of the subject, pulse in a body part of the subject, temperature of an ambient environment of the subject, oxygenation of a body part of the subject, acoustic emission from at least one joint or muscle of the subject, or location of the subject.

10. The garment system of claim 1, wherein the one or more sensors include one or more of an accelerometer, a pedometer, a counter, a tension sensor, a pressure sensor, a torque sensor, a time-keeper, a pulse sensor, a chemical sensor, an oximeter, or a temperature sensor.

11. The garment system of claim 1, wherein the at least one flexible compression garment is substantially tubular and configured to generally conform to the at least one body part; and
    wherein the at least one body part includes at least a portion of an arm, at least a portion of an elbow, at least a portion of a forearm, at least a portion of a wrist, at least a portion of a hand, at least a portion of a thigh, at least a portion of a knee, at least a portion of a lower leg, at least a portion of a foot, at least a portion of a neck, at least a portion of a hip, or at least a portion of a torso.

12. The garment system of claim 1, wherein the at least one flexible compression garment is configured as a limb sleeve, a joint sleeve, a shirt, a vest, a jacket, an undershirt, a girdle, an abdominal support, a back support, gloves, shorts, pants, or socks.

13. The garment system of claim 1, wherein the one or more actuators include at least one of one or more electroactive polymer actuators, one or more electroactive metallic actuators, one or more thermally active polymer actuators, one or more motors, or one or more hydraulic actuators.

14. The garment system of claim 1, wherein the one or more actuators extend circumferentially along the at least one flexible compression garment, and are positioned and configured to increase or decrease the interior space of the at least one flexible compression garment responsive to actuation thereof.

15. The garment system of claim 1, wherein the one or more actuators includes a substantially tubular actuator.

16. The garment system of claim 1, wherein the one or more actuators are at least partially embedded within the flexible compression garment.

17. The garment system of claim 1, wherein the at least one flexible compression garment defines an exterior, and wherein the one or more actuators extend about at least a portion of the exterior of the at least one flexible compression garment.

18. The garment system of claim 1, wherein the control system includes:
    a power supply operably coupled to at least one of the one or more actuators or the control electrical circuitry.

19. The garment system of claim 1, wherein the control electrical circuitry of the control system is configured to direct the one or more actuators to apply a gradient of constriction or dilation responsive to the one or more sensing signals from the one or more sensors.

20. The garment system of claim 1, wherein the control electrical circuitry of the control system is configured to direct the one or more actuators to apply constriction or dilation pulses responsive to the one or more sensing signals from the one or more sensors.

21. The garment system of claim 1, wherein the control circuitry of the control system is configured to direct the one or more actuators to selectively constrict or selectively dilate substantially in cycle with the at least one characteristic sensed by the one or more sensors.

22. The garment system of claim 21, wherein the at least one characteristic includes at least one of pressure exerted on or by a body part of a subject, acceleration of at least a body part of the subject, a pulse at a body part of the subject, heartbeat of the subject, electrical activity of muscles of one or more body parts of the subject, or gait of the subject.

23. The garment system of claim 1, wherein the motion-conducive equipment includes an equipment controller having equipment programming instructions therein and the equipment controller is operably coupled to at least one of the one or more sensors or the control system, the equipment programming instructions being based on one or more movement properties.

24. The garment system of claim 23, wherein at least one of the one or more sensors or the control system is configured to receive an indication signal from the equipment controller that an alteration in one or more movement properties is imminent.

25. The garment system of claim 24, wherein the one or more movement properties includes at least one of an angle of incline of the motion-conducive equipment, resistance of the motion-conducive equipment, duration of a movement, or path of motion of a movement.

26. The garment system of claim 1, wherein the control system includes memory configured to store sensing data corresponding to the one or more sensing signals and actuation data corresponding to selective constriction or selective dilation of the at least one flexible compression garment.

27. The garment system of claim 1, wherein the control electrical circuitry of the control system is configured to direct the one or more actuators to selectively constrict responsive to the one or more sensing signals from the one or more sensors being indicative of the at least one characteristic being below or above a threshold level.

28. The garment system of claim 27, wherein the threshold level includes at least one of an acceleration threshold level of the subject, a threshold level of load applied to the one or more sensors by a body part of the subject, a threshold level of pressure applied to the one or more sensors by a body part of the subject, a threshold level of tension applied to the one or more sensors by a body part of the subject, a pulse threshold level of the subject, a time threshold level, an oxygen threshold level of the subject, a chemical threshold level of the subject, an equipment use threshold level for the subject, a travel distance threshold level for the subject, or a temperature threshold level of the subject.

29. The garment system of claim 1, wherein the control electrical circuitry of the control system is configured to direct the one or more actuators to selectively constrict or dilate responsive to the one or more sensing signals from the one or more sensors being indicative of the subject being injured.

30. The garment system of claim 1, wherein the control electrical circuitry of the control system is configured to direct the one or more actuators to selectively constrict or dilate responsive to the one or more sensing signals from the one or more sensors being indicative of passage of a selected amount of time.

31. The garment system of claim 1, wherein the control system includes a user interface through which the control system can be programmed with at least one operational program that controls an amount of selective constriction or selective dilation applied by the one or more actuators.

32. The garment system of claim 1, wherein the control system includes a user interface through which the control system can be programmed with at least one operational program that controls an amount of selective constriction or selective dilation applied by the one or more actuators.

33. A method of selectively controlling a compression garment, the method comprising:
sensing at least one characteristic of a subject moving on at least one piece of motion-conducive equipment using one or more sensors associated therewith;
comparing the sensed at least one characteristic to a threshold characteristic; and
responsive to comparing the at least one characteristic, actuating one or more actuators in at least one flexible compression garment worn on the subject to selectively constrict or selectively dilate on at least one body part of the subject.

34. The method of claim 33 wherein actuating one or more actuators to selectively constrict or selectively dilate includes actuating the one or more actuators during movement of the subject on the at least one piece of motion-conducive equipment.

35. The method of claim 33, wherein sensing at least one characteristic includes sensing at least one of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, a load on a body part of the subject, pressure on a body part of the subject, tension on a body part of the subject, pulse in a body part of the subject, velocity of at least a body part of the subject, acceleration of at least a body part of the subject, velocity of at least a portion of the motion-conducive equipment, acceleration of at least a portion of the motion-conducive equipment, location of the subject, gait of the subject, pace at which the subject moves, distance that the subject has traveled, nerve activity of the subject, chemical excretion of the subject, temperature in a body part of the subject, heart rate of the subject, pulse in a body part of the subject, temperature of an ambient environment of the subject, oxygenation of a body part of the subject, acoustic emission from at least one joint or muscle of the subject, or location of the subject.

36. The method of claim 35, wherein sensing a change in motion of travel of the subject includes sensing one or more of a change in direction of travel of the subject, a change in velocity of the subject, or a change in acceleration of the subject.

37. The method of claim 33, wherein sensing at least one characteristic includes sensing, over a selected period of time, at least one of a change in motion of travel of the subject, a load applied to the one or more sensors by a body part of the subject, pressure applied to the one or more sensors by a body part of the subject, tension applied to the one or more sensors by a body part of the subject, torque applied to the one or more sensors by a body part of the subject, a load on a body part of the subject, pressure on a body part of the subject, tension on a body part of the subject, pulse in a body part of the subject, velocity of at least a body part of the subject, acceleration of at least a body part of the subject, velocity of at least a portion of the motion-conducive equipment, acceleration of at least a portion of the motion-conducive equipment, location of the subject, gait of the subject, pace at which the subject moves, distance that the subject has traveled, nerve activity of the subject, chemical excretion of the subject, temperature in a body part of the subject, heart rate of the subject, pulse in a body part of the subject, temperature of an ambient environment of the subject, oxygenation of a body part of the subject, acoustic emission from at least one joint or muscle of the subject, or location of the subject.

38. The method of claim 37, wherein sensing, over a selected period of time, a change in motion of travel of the subject includes sensing, over period of time, one or more of a change in direction of travel of the subject, a change in velocity of the subject, or a change in acceleration of the subject.

39. The method of claim 33, wherein actuating one or more actuators includes actuating at least one of one or more electroactive polymer actuators, one or more electroactive metallic actuators, one or more thermally active polymer actuators, one or more motors, or one or more hydraulic actuators.

40. The method of claim 33, wherein actuating one or more actuators includes applying a voltage or a current to the one or more actuators to cause actuation thereof.

41. The method of claim 33, wherein actuating one or more actuators is responsive to the at least one characteristic sensed by one or more sensors being indicative of the subject being injured.

42. The method of claim 33, wherein actuating one or more actuators is responsive to the at least one characteristic sensed by the one or more sensors being over or below a threshold level.

43. The method of claim 42, wherein the threshold level includes at least one of an acceleration threshold level of the subject, a threshold level of load applied to the one or more sensors by a body part of the subject, a threshold level of pressure applied to the one or more sensors by a body part of the subject, a threshold level of tension applied to the one or more sensors by a body part of the subject, a pulse threshold level of the subject, a time threshold level, an oxygen threshold level of the subject, a chemical threshold level of the subject, a travel distance threshold level for the subject, an equipment use threshold level for the subject, or a temperature threshold level of the subject.

44. The method of claim 43, wherein the garment system includes a control system operably coupled to the one or more sensors and the one or more actuators, the control system including control electrical circuitry configured to direct the one or more actuators to selectively constrict or dilate responsive to receiving one or more sensing signals from the one or more sensors.

45. The method of claim 44 wherein the motion-conducive equipment includes an equipment controller having equipment programming instructions stored therein, and wherein the equipment controller is operably coupled the control system, the equipment programming instructions being based on one or more movement properties.

46. The method of claim 45, further including, with the control system, directing the equipment controller to alter one or more movement properties or stop operation of the motion-conducive equipment responsive to one or more sensing signals.

47. The method of claim 46, further including, at the control system, receiving an indication signal from the equipment controller that an alteration in one or more movement properties is imminent.

48. The method of claim 45, further including, with the control system, directing the equipment controller to alter one or more movement properties and actuate one or more actuators responsive to one or more sensing signals.

49. The method of claim 33, wherein actuating one or more actuators occurs according to at least one pre-programmed operational program.

50. The method of claim 49 wherein the at least one pre-programmed operational program is related to at least one selected profile.

51. The method of claim 50, wherein the at least one selected profile includes one or more of subject age, subject preferences, a target pace, a target pulse, a target distance of travel, a duration of movement, or an intensity of movement.

52. The method of claim 49, wherein the at least one pre-programmed operational program is selected from multiple operational programs having one or more different actuation criteria, pulse constriction or dilation rates, constriction or dilation strengths, or constriction or dilation durations.

53. The method of claim 33, wherein actuating one or more actuators includes actuating the one or more actuators substantially in cycle with the at least one characteristic sensed by the one or more sensors.

54. The method of claim 53, wherein the at least one characteristic includes at least one of pulse in a body part of the subject, heartbeat of the subject, repetitive motion of the subject, or gait of the subject.

55. The method of claim 33, further including storing, in memory, sensing signals from the one or more sensors and actuation data corresponding to selective constriction or the selective dilation of the at least one flexible compression garment.

56. The method of claim 33, wherein actuating one or more actuators includes directing the at least one flexible compression garment to selectively constrict or dilate in substantial concert with one or more of a sensed pulse of the subject, a gait of the subject, an increase in muscle tension of the subject, a change in direction of the subject, a change in acceleration of the subject, a change in velocity of the subject, or a force applied to the one or more sensors by a body part of the subject.

* * * * *